（12）United States Patent
Kim et al.

(10) Patent No.: US 9,684,335 B2
(45) Date of Patent: Jun. 20, 2017

(54) ROTARY DEVICE AND ELECTRONIC DEVICE HAVING THE SAME

(71) Applicant: Samsung Electronics Co., Ltd., Gyeonggi-do (KR)

(72) Inventors: Jonghae Kim, Seoul (KR); Youngsun Park, Gyeonggi-do (KR)

(73) Assignee: Samsung Electronics Co., Ltd., Yeongtong-gu, Suwon-si, Gyeonggi-do (KR)

( * ) Notice: Subject to any disclaimer, the term of this patent is extended or adjusted under 35 U.S.C. 154(b) by 27 days.

(21) Appl. No.: 14/805,790

(22) Filed: Jul. 22, 2015

(65) Prior Publication Data

US 2016/0060926 A1    Mar. 3, 2016

(30) Foreign Application Priority Data

Aug. 26, 2014    (KR) .................. 10-2014-0111832

(51) Int. Cl.
*G06F 1/16*    (2006.01)
*G03B 17/56*    (2006.01)
(Continued)

(52) U.S. Cl.
CPC ........... *G06F 1/163* (2013.01); *F16M 11/105* (2013.01); *F16M 13/02* (2013.01); *F16M 13/04* (2013.01);
(Continued)

(58) Field of Classification Search
CPC .... G06F 1/163; H04R 1/1066; A61B 5/02438
(Continued)

(56) References Cited

U.S. PATENT DOCUMENTS 6,034,653 A * 3/2000 Robertson .......... G02B 27/0176
345/8
7,310,072 B2* 12/2007 Ronzani ............... G02B 27/017
345/102
(Continued)

FOREIGN PATENT DOCUMENTS

JP    2002-306553 A    10/2002
JP    2003-240542 A    8/2003
(Continued)

*Primary Examiner* — Nidhi Thaker
(74) *Attorney, Agent, or Firm* — Cha & Reiter, LLC

(57) ABSTRACT

A rotary device may include: a binding unit detachably coupled to a part of an external object and including a side surface defining a geometric plane and having a length through which a longitudinal axis extends; a stationary unit positioned adjacent to the side surface of the binding unit and formed integrally with or coupled to the binding unit; and a rotary unit coupled to the stationary unit, the rotary unit including a first end and a second end, the first and second ends being opposite one another, the first end being rotatably coupled to the stationary unit, wherein the rotary unit is rotatable between a first position where the rotary unit forms a first angle with respect to the longitudinal axis and a second position where the rotary unit forms a second angle with the respect to the longitudinal axis, wherein at the first position, the second end of the rotary unit is a first distance from the geometric plane, and wherein at the second position, the second end of the rotary unit is a second distance from the geometric plane, the second distance being different from the first distance.

23 Claims, 19 Drawing Sheets

(51) Int. Cl.
  *F16M 13/04* (2006.01)
  *H04R 1/10* (2006.01)
  *F16M 11/10* (2006.01)
  *F16M 13/02* (2006.01)
  *A61B 5/024* (2006.01)

(52) U.S. Cl.
  CPC ......... *G03B 17/561* (2013.01); *H04R 1/1066* (2013.01); *A61B 5/02438* (2013.01); *H04R 1/1041* (2013.01); *H04R 2201/025* (2013.01)

(58) Field of Classification Search
  USPC .................................... 361/679.03, 679.55
  See application file for complete search history.

(56) References Cited

U.S. PATENT DOCUMENTS

| | | | |
|---|---|---|---|
| 7,539,525 B2 | 5/2009 | Kim | |
| 7,798,638 B2* | 9/2010 | Fuziak, Jr. | G02B 27/0172 345/7 |
| 7,988,283 B2 | 8/2011 | Jannard | |
| 8,200,289 B2* | 6/2012 | Joo | G06F 1/1616 379/430 |
| 2004/0130658 A1* | 7/2004 | Yamaguchi | G06F 1/1616 348/375 |
| 2005/0058280 A1 | 3/2005 | Ma | |
| 2007/0145149 A1* | 6/2007 | Carnevali | G06F 1/163 235/486 |
| 2007/0195515 A1 | 8/2007 | Waters | |
| 2008/0291277 A1* | 11/2008 | Jacobsen | G02B 27/0172 348/158 |
| 2009/0156990 A1* | 6/2009 | Wenger | A61M 5/14244 604/67 |
| 2012/0212398 A1* | 8/2012 | Border | G02B 27/017 345/8 |
| 2013/0188080 A1* | 7/2013 | Olsson | G09G 5/00 348/333.01 |
| 2015/0029227 A1* | 1/2015 | Park | G06F 1/163 345/659 |
| 2015/0185763 A1* | 7/2015 | Idsinga | G06F 1/163 361/679.03 |

FOREIGN PATENT DOCUMENTS

| | | |
|---|---|---|
| JP | 2008-102466 A | 5/2008 |
| KR | 10-2006-0062958 A | 6/2006 |
| KR | 10-0630126 B1 | 9/2006 |
| KR | 10-2008-0011504 A | 2/2008 |
| KR | 10-0865959 B1 | 10/2008 |

* cited by examiner

ROTARY DEVICE AND ELECTRONIC DEVICE HAVING THE SAME

CLAIM OF PRIORITY

This application claims the benefit under 35 U.S.C. §119(a) of Korean patent application filed on Aug. 26, 2014 in the Korean Intellectual Property Office and assigned Serial number 10-2014-0111832, the entire disclosure of which is hereby incorporated by reference.

TECHNICAL FIELD

The present disclosure relate to a rotary device and an electronic device including the same, and more particularly, to a rotary device capable of being detachably attached to a device, such as eyeglasses, by a user who uses eyeglasses.

BACKGROUND

Due to the advancement of electronic techniques, various wearable devices are being developed. The wearable devices are worn on a user's body to be capable of providing various functions to the user. For example, there is an increasing developing effort to implement, for example, a game, music, multimedia contents, or an application that is usable in an existing electronic device, in a wearable device. Further, in consideration of the fact that the wearable device is used in a state where it is positioned close to the user's body, research and development to mount various sensors on a wearable device are actively on the way.

A conventional headset requires a separate device in order to fix it to a user's body. The separate device is used in a state where it is put on, for example, the user's head or neck, which may cause the user to feel inconvenience.

In addition, when the headset is not used, the headset is carried in a state where it is completely separated from the user's body. However, since the device to fix the headset to the user's head or neck has a large volume, there is a problem in that the portability is poor.

In order to solve this problem, for example, an earphone or earpiece or earbud or the like that typically rest on or within a user's inner ears, and have a relatively smaller size than headsets that typically rest on or over the user's outer ears, may be used instead of headsets. Although earphones have become increasingly smaller in size, when the earphones are not in use, there is still a problem of portability because there is no convenient place to store the earphones when not in use. In particular, when in the ear, the earphones are easily carried, but when not in use, the earphones are separated from the user's body and must be held or separately carried. Thus, both earphones and headsets present problems to the user in terms of their being portable. As used herein, the term headset or earphone or the like may be used interchangeably and may generally refer to any of the following: headsets, headphones, earphones, and the like.

SUMMARY

The present disclosure relates to improving the usability and portability of an electronic device (e.g., a Bluetooth headset, a heart rate monitor, or other sensors) including a sound module or various sensors, and to allow a user using, for example, eyeglasses, to conveniently use the electronic device detachably attached to a part of the user's body.

In accordance with an aspect of the present disclosure, a rotary device is provided. The rotary device may include: a binding unit configured to be detachably attached to a part of an external object and including a side surface; a stationary unit positioned adjacent to the side surface of the binding unit. The stationary unit may be formed integrally with or coupled to the binding unit. A rotary unit may be coupled to the stationary unit to be at least partially rotatable with respect to the stationary unit. The rotary unit may be rotatable between a first position where the rotary unit forms a first angle with respect to a longitudinal axis extending through a part of the external object and a second position where the rotary unit forms a second angle with respect to the longitudinal axis extending through the part of the external object, at the first position. In the first position, the rotary unit may be a first distance from a geometric plane including the side surface, and at the second position, the rotary unit be a second distance from the plane including the side surface. The second distance being different from the first distance.

In accordance with another aspect of the present disclosure, an electronic device comprising a rotary device is provided. The rotary device may include: a binding unit configured to be coupled to an external object. A stationary unit may be coupled to the binding unit, a rotary unit may be coupled to the stationary unit. The rotary may be configured to be fixed among a plurality of set positions. For example, as the rotary unit is rotated with respect to the stationary unit, the rotary unit is sequentially moved toward or away from the binding unit at the plurality of positions. The rotary device may include a main body coupled to the rotary unit, and the main body includes a coupling part coupled to the rotary unit, and a first module or a second module mounted thereon.

These and other features of the present disclosure will be more fully described hereinbelow with reference to the accompanying figures.

BRIEF DESCRIPTION OF THE DRAWINGS

The above and other aspects, features, and advantages of certain embodiments of the present disclosure will be more apparent from the following detailed description taken in conjunction with the accompanying drawings, in which.

DETAILED DESCRIPTION

Figure 1:
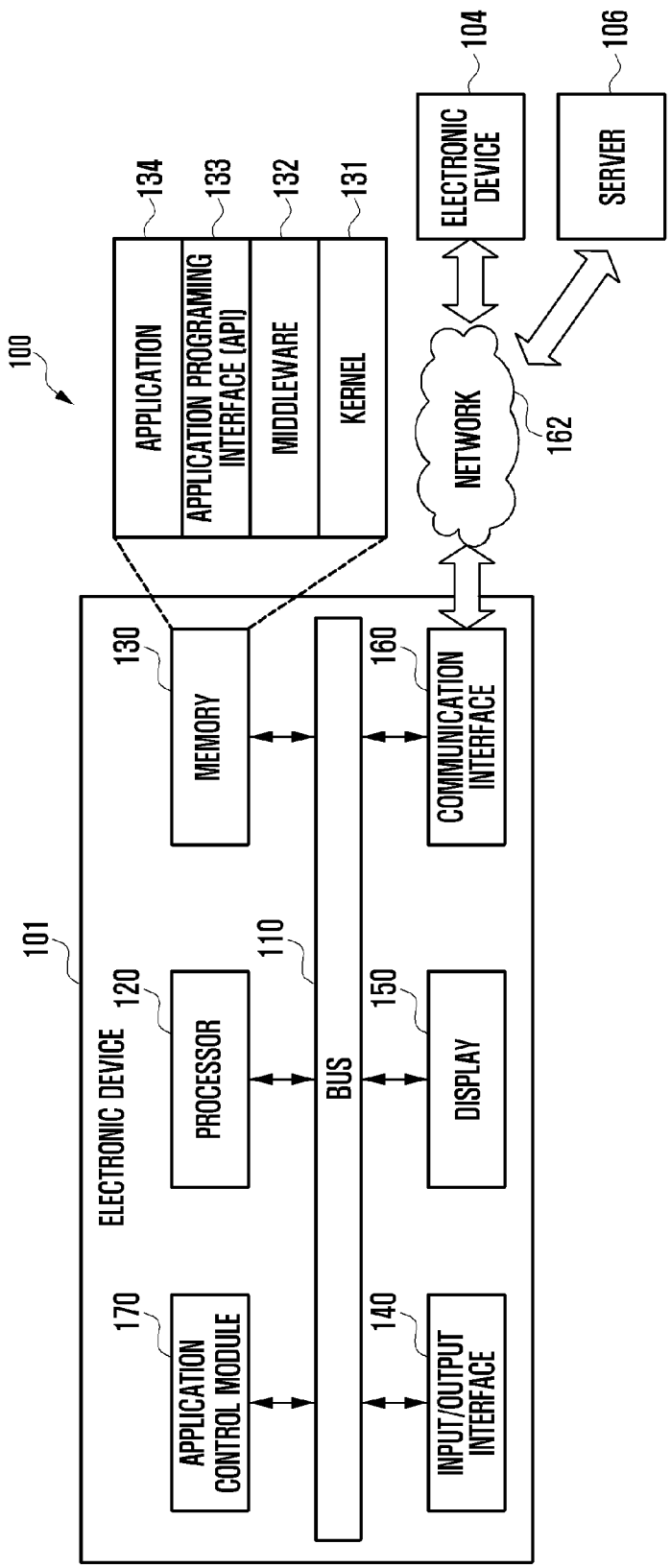
FIG. 1 is a view illustrating a network environment including an electronic device according to various embodiments of the present disclosure.

Hereinafter, the present disclosure will be described with reference to the accompanying drawings. The present disclosure may have various embodiments, and modifications and changes may be made therein. Therefore, the present disclosure will be described in detail with reference to particular embodiments shown in the accompanying drawings. However, it should be understood that there is no intent to limit the present disclosure to the particular forms, and the present disclosure should be construed to cover all modifications, equivalents, and/or alternatives falling within the spirit and scope of the present disclosure. In describing the drawings, similar elements are designated by similar reference numerals.

As used in the present disclosure, the expression "include" or "may include" or "can include" refers to the existence of a corresponding function, operation, or constituent element, and does not limit one or more additional functions, operations, or constituent elements. Further, as used in the present disclosure, the term such as "include" or "have" may be construed to denote a certain characteristic, number, step, operation, constituent element, component or a combination thereof, but may not be construed to exclude the existence of or a possibility of addition of one or more other characteristics, numbers, steps, operations, constituent elements, components or combinations thereof.

As used in the present disclosure, the expression "and/or" includes any or all combinations of words enumerated together. For example, the expression "A or B" or "at least one of A and B" may include A, may include B, or may include both A and B.

While expressions including ordinal numbers, such as "first" and "second", as used in the present disclosure may modify various constituent elements, such constituent elements are not limited by the above expressions. For example, the above expressions do not limit the sequence and/or importance of the corresponding constituent elements. The above expressions may be used merely for the purpose of distinguishing a constituent element from other constituent elements. For example, a first user device and a second user device indicate different user devices although both are user devices. For example, a first constituent element may be termed a second constituent element, and likewise a second constituent element may also be termed a first constituent element without departing from the scope of the present disclosure.

When a component is referred to as being "connected" or "accessed" to any other component, it should be understood that the component may be directly connected or accessed to the other component, but another new component may also be interposed between them. Contrarily, when a component is referred to as being "directly connected" or "directly accessed" to any other component, it should be understood that there is no new component between the component and the other component.

The terms as used in various embodiments of the present disclosure are merely for the purpose of describing particular embodiments and are not intended to limit the present disclosure. Singular forms are intended to include plural forms unless the context clearly indicates otherwise.

Unless defined otherwise, all terms used herein, including technical terms and scientific terms, have the same meaning as commonly understood by a person of ordinary skill in the art to which the present disclosure pertains. Such terms as those defined in a generally used dictionary are to be interpreted to have the meanings equal to the contextual meanings in the relevant field of art, and are not to be interpreted to have ideal or excessively formal meanings unless clearly defined in the present disclosure.

In this disclosure, an electronic device may be a device that performs a communication function. For example, an electronic device may be a smart phone, a tablet PC (Personal Computer), a mobile phone, a video phone, an e-book reader, a desktop PC, a laptop PC, a netbook computer, a PDA (Personal Digital Assistant), a PMP (Portable Multimedia Player), an MP3 player, a portable medical device, a digital camera, or a wearable device (e.g., an HMD (Head-Mounted Device) such as, for example, electronic glasses, electronic clothes, an electronic bracelet, an electronic necklace, electronic tattoos, an electronic accessory, or a smart watch).

According to various embodiments, an electronic device may be a smart home appliance that performs a communication function. For example, an electronic device may be a TV, a DVD (Digital Video Disk) player, audio equipment, a refrigerator, an air conditioner, a vacuum cleaner, an oven, a microwave, a washing machine, an air cleaner, a set-top box, a TV box (e.g., Samsung HomeSync™, Apple TV™, Google TV™, etc.), a game console, an electronic dictionary, an electronic key, a camcorder, or an electronic picture frame.

According to various embodiments, an electronic device may be a medical device (e.g., MRA (Magnetic Resonance Angiography), MRI (Magnetic Resonance Imaging), CT (Computed Tomography), ultrasonography, etc.), a navigation device, a GPS (Global Positioning System) receiver, an EDR (Event Data Recorder), an FDR (Flight Data Recorder), a car infotainment device, electronic equipment for ship (e.g., a marine navigation system, a gyrocompass, etc.), avionics, security equipment, or an industrial or home robot, robot, an automatic teller machine of financial institutions, or point of sales of stores.

According to various embodiments, an electronic device may be furniture or part of a building or construction having a communication function, an electronic board, an electronic signature receiving device, a projector, or various measuring instruments (e.g., a water meter, an electric meter, a gas meter, a wave meter, etc.). An electronic device disclosed herein may be one of the above-mentioned devices or any combination thereof. Further, the electronic device according to the present disclosure may be a flexible device. It is noted that the above-mentioned electronic devices are exemplary only and not to be considered as a limitation of this disclosure.

Hereinafter, an electronic device according to various embodiments of the present disclosure will be discussed with reference to the accompanying drawings. The term "a user" as used in various embodiments may refer to any person who uses an electronic device or any other device (e.g., an artificial intelligence electronic device) using an electronic device.

FIG. 1 is a block diagram illustrating a network environment 100 including therein an electronic device 101 in accordance with an embodiment of the present disclosure. The electronic device 101 may include, but is not limited to, a bus 110, a processor 120, a tangible, non-transitory, computer readable medium or memory 130, an input/output interface 140, a display 150, a communication interface 160, and/or an application control module 170.

The bus 110 may be a circuit designed for connecting the above-discussed elements and communicating data (e.g., a control message) between such elements.

The processor 120 may receive commands from the other elements (e.g., the memory 130, the input/output interface 140, the display 150, the communication interface 160, or the application control module 170, etc.) through the bus 110. The processor 120 may interpret the received commands, and perform arithmetic or data processing based on the interpreted commands.

The memory 130 may store therein commands or data received from or created by the processor 120 or other elements (e.g., the input/output interface 140, the display 150, the communication interface 160, or the application control module 170, etc.). The memory 130 may include programming modules such as a kernel 131, a middleware 132, an application programming interface (API) 133, and an application 134. Each of the programming modules may be composed of software, firmware, hardware, and/or any combination thereof.

The kernel 131 may control or manage system resources (e.g., the bus 110, the processor 120, or the memory 130, etc.) used for performing operations or functions of the other programming modules, e.g., the middleware 132, the API 133, or the application 134. Additionally, the kernel 131 may offer an interface that allows the middleware 132, the API 133 or the application 134 to access, control and/or manage individual elements of the electronic device 101.

The middleware 132 may perform intermediation by which the API 133 or the application 134 communicates with the kernel 131 to transmit or receive data. Additionally, in connection with task requests received from the applications 134, the middleware 132 may perform a control (e.g., scheduling or load balancing) for the task request by using technique such as assigning the priority for using a system resource of the electronic device 101 (e.g., the bus 110, the processor 120, or the memory 130, etc.) to at least one of the applications 134.

The API 133, which is an interface for allowing the application 134 to control a function provided by the kernel 131 or the middleware 132, may include, for example, at least one interface or function (e.g., a command) for a file control, a window control, an image processing, a text control, and the like.

According to various embodiments, the application 134 may include an SMS/MMS application, an email application, a calendar application, an alarm application, a health care application (e.g., an application for measuring quantity of motion or blood sugar), an environment information application (e.g., an application for offering information about atmospheric pressure, humidity, or temperature, etc.), and the like. The application 134 may be an application associated with an exchange of information between the electronic device 101 and any external electronic device (e.g., an external electronic device 104). This type of application may include a notification relay application, which may deliver specific information to an external electronic device, or a device management application for managing an external electronic device.

For example, the notification relay application may include a function to deliver notification information created at any other application of the electronic device 101 (e.g., the SMS/MMS application, the email application, the health care application, or the environment information application, etc.) to an external electronic device (e.g., the electronic device 104). The notification relay application may receive notification information from an external electronic device and offer it to a user. The device management application may manage (e.g., install, remove or update) a certain function (a turn-on/turn-off of an external electronic device (or some components thereof), or an adjustment of brightness (or resolution) of a display) of any external electronic device communicating with the electronic device 101, a certain application operating at such an external electronic device, or a certain service (e.g., a call service or a message service) offered by such an external electronic device.

According to embodiments, the application 134 may include a specific application specified depending on attributes (e.g., a type) of an external electronic device (e.g., the electronic device 104). For example, in case an external electronic device is an MP3 player, the application 134 may include a specific application associated with a play of music. Similarly, when an external electronic device is a portable medical device, the application 134 may include a specific application associated with health care. In an embodiment, the application 134 may include at least one of an application assigned to the electronic device 101 or an application received from an external electronic device (e.g., the server 106 or the electronic device 104).

The input/output interface 140 may deliver commands or data, entered by a user through an input/output unit (e.g., a sensor, a keyboard, or a touch screen), to the processor 120, the memory 130, the communication interface 160, or the application control module 170 via the bus 110. For example, the input/output interface 140 may offer data about a user's touch, entered through the touch screen, to the processor 120. Also, through the input/output unit (e.g., a speaker or a display), the input/output interface 140 may output commands or data, received from the processor 120, the memory 130, the communication interface 160, or the application control module 170 via the bus 110. For example, the input/output interface 140 may output voice data, processed through the processor 120, to a user through the speaker.

The display 150 may display thereon various types of information (e.g., multimedia data, text data, etc.) to a user.

The communication interface 160 may perform a communication between the electronic device 101 and any external electronic device (e.g., the electronic device 104 of the server 106). For example, the communication interface 160 may communicate with any external device by being connected with a network 162 through wired or wireless communication. Wireless communication may include at least one of WiFi (Wireless Fidelity), BT (Bluetooth), NFC (Near Field Communication), GPS (Global Positioning System), or a cellular communication (e.g., LTE, LTE-A, CDMA, WCDMA, UMTS, WiBro, or GSM, etc.). Wired communication may include at least one of USB (Universal Serial Bus), HDMI (High Definition Multimedia Interface), RS-232 (Recommended Standard 232), or POTS (Plain Old Telephone Service).

According to an embodiment, the network 162 may be a communication network, which may include at least one of a computer network, an internet, an internet of things, or a telephone network. According to an embodiment, a protocol (e.g., transport layer protocol, data link layer protocol, or physical layer protocol) for a communication between the electronic device 101 and any external device may be supported by at least one of the application 134, the API 133, the middleware 132, the kernel 131, and/or the communication interface 160.

The application control module 170 may process at least part of information obtained from the other elements (e.g., the processor 120, the memory 130, the input/output interface 140, or the communication interface 160, etc.) and then offer it to a user in various ways. For example, the application control module 170 may recognize information about access components equipped in the electronic device 101, store such information in the memory 130. The application 134 may be executed on the basis of such information.

Figure 2:
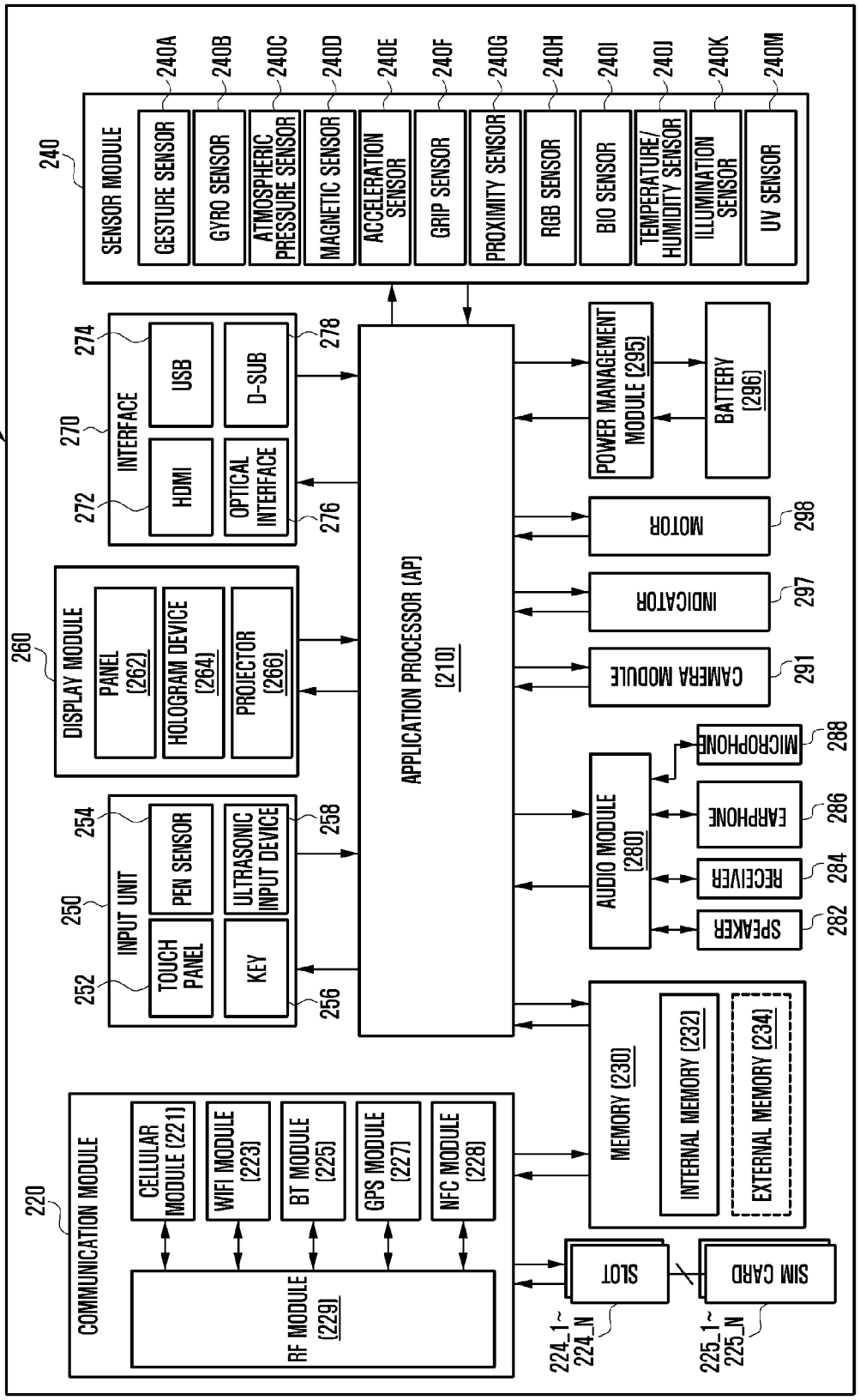
FIG. 2 is a block diagram of an electronic device according to various embodiments of the present disclosure.

FIG. 2 is a block diagram illustrating an electronic device 201 in accordance with an embodiment of the present disclosure. The electronic device 201 may form, for example, the whole or part of the electronic device 101 shown in FIG. 1. Electronic device 201 may include at least one application processor (AP) 210, a communication module 220, a subscriber identification module (SIM) card 224, a memory 230, a sensor module 240, an input unit 250, a display 260, an interface 270, an audio module 280, a camera module 291, a power management module 295, a battery 296, an indicator 297, and a motor 298.

The AP 210 may drive an operating system or applications, control a plurality of hardware or software components connected thereto, and also perform processing and operation for various data including multimedia data. The AP 210 may be formed, for example, of system-on-chip (SoC). According to an embodiment, the AP 210 may further include a graphic processing unit (GPU).

The communication module 220 (e.g., the communication interface 160) may perform data communication with any other electronic device (e.g., the electronic device 104 or the server 106) connected to the electronic device 200 (e.g., the electronic device 101) through the network. According to an embodiment, the communication module 220 may include therein a cellular module 221, a WiFi module 223, a BT module 225, a GPS module 227, an NFC module 228, and/or an RF (Radio Frequency) module 229.

The cellular module 221 may support a voice call, a video call, a message service, an internet service, or the like through a communication network (e.g., LTE, LTE-A, CDMA, WCDMA, UMTS, WiBro, or GSM, etc.). Additionally, the cellular module 221 may perform identification and authentication of the electronic device in the communication network, using the SIM card 224. According to an embodiment, the cellular module 221 may perform at least part of functions the AP 210 can provide. For example, the cellular module 221 may perform at least part of a multimedia control function.

According to an embodiment, the cellular module 221 may include a communication processor (CP). Additionally, the cellular module 221 may be formed of SoC, for example. Although some elements such as the cellular module 221 (e.g., the CP), the memory 230, or the power management module 295 are shown as separate elements being different from the AP 210 in FIG. 2, the AP 210 may be formed to have at least part (e.g., the cellular module 221) of the above elements in an embodiment.

According to an embodiment, the AP 210 or the cellular module 221 (e.g., the CP) may load commands or data, received from a nonvolatile memory connected thereto or from at least one of the other elements, into a volatile memory to process them. Additionally, the AP 210 or the cellular module 221 may store data, received from or created at one or more of the other elements, in the nonvolatile memory.

Each of the WiFi module 223, the BT module 225, the GPS module 227 and the NFC module 228 may include a processor for processing data transmitted or received therethrough. Although FIG. 2 shows the cellular module 221, the WiFi module 223, the BT module 225, the GPS module 227 and the NFC module 228 as different blocks, at least part of them may be contained in a single IC (Integrated Circuit) chip or a single IC package in an embodiment. For example, at least part (e.g., the CP corresponding to the cellular module 221 and a WiFi processor corresponding to the WiFi module 223) of respective processors corresponding to the cellular module 221, the WiFi module 223, the BT module 225, the GPS module 227 and the NFC module 228 may be formed as a single SoC.

The RF module 229 may transmit and receive data, e.g., RF signals or any other electric signals. Although not shown, the RF module 229 may include a transceiver, a PAM (Power Amp Module), a frequency filter, an LNA (Low Noise Amplifier), or the like. Also, the RF module 229 may include any component, e.g., a wire or a conductor, for transmission of electromagnetic waves in a free air space. Although FIG. 2 shows that the cellular module 221, the WiFi module 223, the BT module 225, the GPS module 227 and the NFC module 228 share the RF module 229, at least one of them may perform transmission and reception of RF signals through a separate RF module in an embodiment.

The SIM card 224_1 to 224_N may be a specific card formed of SIM and may be inserted into a slot 225_1 to 225_N formed at a certain place of the electronic device. The SIM card 224_1 to 224_N may contain therein an ICCID (Integrated Circuit Card Identifier) or an IMSI (International Mobile Subscriber Identity).

The memory 230 (e.g., the memory 130) may include an internal memory 232 and an external memory 234. The internal memory 232 may include, for example, at least one of a volatile memory (e.g., DRAM (Dynamic RAM), SRAM (Static RAM), SDRAM (Synchronous DRAM), etc.) or a nonvolatile memory (e.g., OTPROM (One Time Programmable ROM), PROM (Programmable ROM), EPROM (Erasable and Programmable ROM), EEPROM (Electrically Erasable and Programmable ROM), mask ROM, flash ROM, NAND flash memory, NOR flash memory, etc.).

According to an embodiment, the internal memory 232 may have the form of an SSD (Solid State Drive). The external memory 234 may include a flash drive, e.g., CF (Compact Flash), SD (Secure Digital), Micro-SD (Micro Secure Digital), Mini-SD (Mini Secure Digital), xD (Extreme Digital), memory stick, or the like. The external memory 234 may be functionally connected to the electronic device 200 through various interfaces. According to an embodiment, the electronic device 200 may further include a storage device or medium such as a hard drive.

The sensor module 240 may measure physical quantity or sense an operating status of the electronic device 200, and then convert measured or sensed information into electrical signals. The sensor module 240 may include, for example, at least one of a gesture sensor 240A, a gyro sensor 240B, an atmospheric sensor 240C, a magnetic sensor 240D, an acceleration sensor 240E, a grip sensor 240F, a proximity sensor 240G, a color sensor 240H (e.g., RGB (Red, Green, Blue) sensor), a biometric sensor 240I, a temperature-humidity sensor 240J, an illumination sensor 240K, and a UV (ultraviolet) sensor 240M. Additionally or alternatively, the sensor module 240 may include, e.g., an E-nose sensor (not shown), an EMG (electromyography) sensor (not shown), an EEG (electroencephalogram) sensor (not shown), an ECG (electrocardiogram) sensor (not shown), an IR (infrared) sensor (not shown), an iris scan sensor (not shown), or a finger scan sensor (not shown). Also, the sensor module 240 may include a control circuit for controlling one or more sensors equipped therein.

The input unit 250 may include a touch panel 252, a digital pen sensor 254, a key 256, and/or an ultrasonic input unit 258. The touch panel 252 may recognize a touch input in a manner of capacitive type, resistive type, infrared type, or ultrasonic type. Also, the touch panel 252 may further include a control circuit. In case of a capacitive type, physical contact or proximity may be recognized. The touch panel 252 may further include a tactile layer. In this case, the touch panel 252 may offer a tactile feedback to a user.

The digital pen sensor 254 may be formed in the same or similar manner as receiving a touch input or by using a separate recognition sheet. The key 256 may include, for example, a physical button, an optical key, or a keypad. The ultrasonic input unit 258 is a specific device capable of identifying data by sensing sound waves with a microphone 288 in the electronic device 200 through an input tool that generates ultrasonic signals, thus allowing wireless recognition. According to an embodiment, the electronic device 200 may receive a user input from any external device (e.g., a computer or a server) connected or coupled thereto through the communication module 220.

The display 260 (e.g., the display 150) may include a panel 262, a hologram 264, or a projector 266. The panel 262 may be, for example, LCD (Liquid Crystal Display), AM-OLED (Active Matrix Organic Light Emitting Diode), or the like. The panel 262 may have a flexible, transparent or wearable form. The panel 262 may be formed of a single module with the touch panel 252. The hologram 264 may show a stereoscopic image in the air using interference of light. The projector 266 may project an image onto a screen, which may be located at the inside or outside of the electronic device 200. According to an embodiment, the display 260 may further include a control circuit for controlling the panel 262, the hologram 264, and the projector 266.

The interface 270 may include, for example, an HDMI (High-Definition Multimedia Interface) 272, a USB (Universal Serial Bus) 274, an optical interface 276, or a D-sub (D-subminiature) 278. The interface 270 may be contained, for example, in the communication interface 160 shown in FIG. 1. Additionally or alternatively, the interface 270 may include, for example, an MHL (Mobile High-definition Link) interface, an SD (Secure Digital) card/MMC (Multi-Media Card) interface, or an IrDA (Infrared Data Association) interface.

The audio module 280 may perform a conversion between sounds and electric signals. At least part of the audio module 280 may be contained, for example, in the input/output interface 140 shown in FIG. 1. The audio module 280 may process sound information inputted or outputted through a speaker 282, a receiver 284, an earphone 286, or a microphone 288.

The camera module 291 is a device capable of obtaining still images and moving images. According to an embodiment, the camera module 291 may include at least one image sensor (e.g., a front sensor or a rear sensor), a lens (not shown), an ISP (Image Signal Processor, not shown), or a flash (e.g., LED or xenon lamp, not shown).

The power management module 295 may manage electrical power of the electronic device 200. Although not shown, the power management module 295 may include, for example, a PMIC (Power Management Integrated Circuit), a charger IC, or a battery or fuel gauge.

The PMIC may be formed, for example, of an IC chip or SoC. Charging may be performed in a wired or wireless manner. The charger IC may charge a battery 296 and prevent overvoltage or overcurrent from a charger. According to an embodiment, the charger IC may have a charger IC used for at least one of wired and wireless charging types. A wireless charging type may include, for example, a magnetic resonance type, a magnetic induction type, or an electromagnetic type. Any additional circuit for a wireless charging may be further used such as a coil loop, a resonance circuit, or a rectifier.

The battery gauge may measure the residual amount of power stored in the battery 296 and a voltage, current or temperature in a charging process. The battery 296 may store or create electrical power therein and supply electrical power to the electronic device 200. The battery 296 may be, for example, a rechargeable battery or a solar battery.

The indicator 297 may show thereon a current status (e.g., a booting status, a message status, or a recharging status) of the electronic device 200 or of its part (e.g., the AP 210). The motor 298 may convert an electrical signal into a mechanical vibration. Although not shown, the electronic device 200 may include a specific processor (e.g., GPU) for supporting a mobile TV. This processor may process media data that comply with standards of DMB (Digital Multimedia Broadcasting), DVB (Digital Video Broadcasting), or media flow.

Each of the above-discussed elements of the electronic device disclosed herein may be formed of one or more components, and its name may be varied according to the type of the electronic device. The electronic device disclosed herein may be formed of at least one of the above-discussed elements without some elements or with additional other elements. Some of the elements may be integrated into a single entity that still performs the same functions as those of such elements before integrated.

The term "module" used in this disclosure may refer to a certain unit that includes one of hardware, software and firmware or any combination thereof. The module may be interchangeably used with unit, logic, logical block, component, or circuit, for example. The module may be the minimum unit, or part thereof, which performs one or more particular functions. The module may be formed mechanically or electronically. For example, the module disclosed herein may include at least one of ASIC (Application-Specific Integrated Circuit) chip, FPGAs (Field-Programmable Gate Arrays), and programmable-logic device, which have been known or are to be developed.

Figure 3:
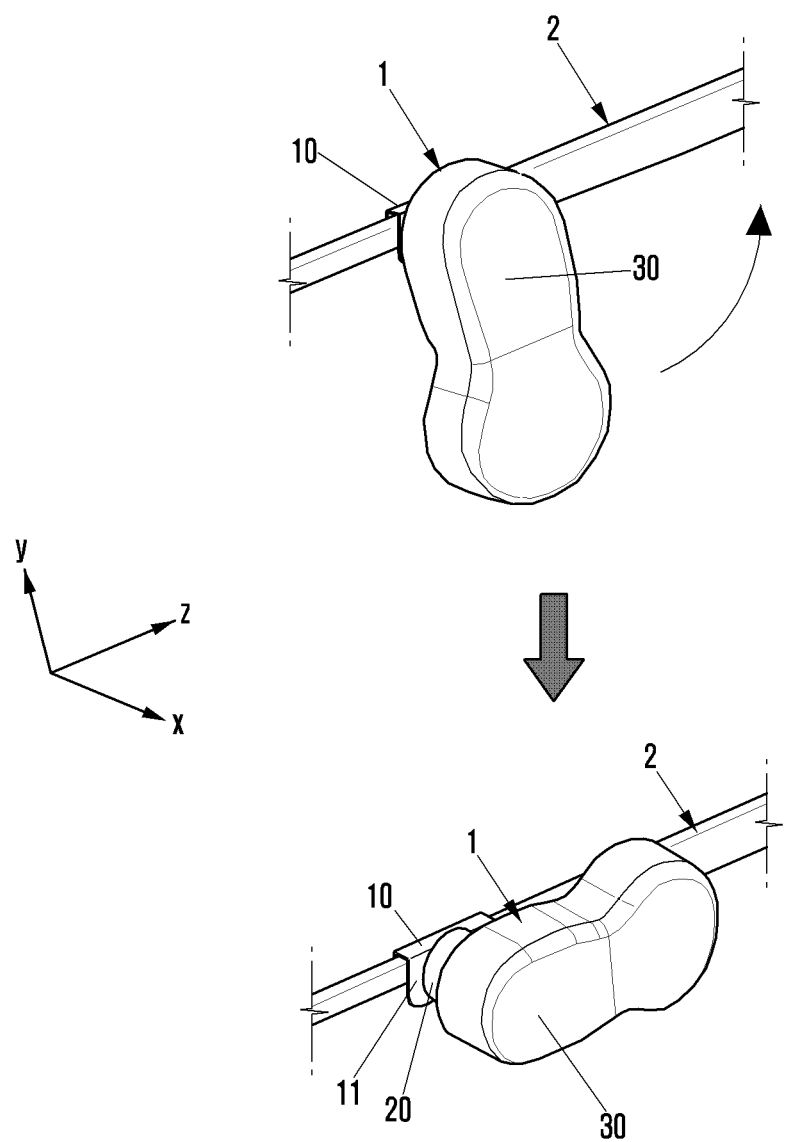
FIG. 3 is a view of a rotary device in a use state according to various embodiments according to the present disclosure.

FIG. 3 is a view for describing a use state of a rotary device 1 according to various embodiments according to the present disclosure.

According to various embodiments according to the present disclosure, a rotary device 1 is capable of being detachably attached to an external object 2 such as a temple of an eyeglass frame. The rotary device 1 may include a binding unit 10, a stationary unit 20, and/or a main body 30.

The binding unit 10 may be capable of being detachably attached to a part of the external object 2, and may include a side surface 11.

The stationary unit 20 is positioned adjacent to the side surface 11 of the binding unit 10 and may be formed integrally with or connected to the binding unit 10.

The main body 30 may be connected to the stationary unit 20 to be at least partially rotatable.

The rotary device 1 may be rotated between a plurality of set positions in a state where it is coupled to the external object 2. FIG. 3 illustrates that the main body 30 is rotated about one axis. At the plurality of positions, the free rotation of the main body 30 is restricted to be fixed in position, and the main body 30 is capable of being rotated only when a predetermined external force is applied thereto.

The main body 30 may be rotatable between a first position where the main body 30 forms a first angle with a portion of the external object 2 and a second position where the main body 30 forms a second angle with the portion of the external object 2.

At the first position, the main body 30 may have a first distance with respect to a plane including to the side surface 11. At the second position, the main body 30 may have a second distance with respect to the plane including the side surface 11. The second distance may be different from the first distance.

According to one embodiment, the rotary device 1 may further include an additional module formed as a separate component that is fixed to or connected to the main body 30. The main body 30 may include an electronic part of the additional module. The additional module may be, for example, a sound module, a Heart Rate Monitor (HRM), or any of various other sensors. The sound module may be an earphone or a bone conduction speaker, etc.

At the first position, the longitudinal direction of the main body 30 may be substantially parallel with the longitudinal direction of the external object 2.

At the second position, the longitudinal direction of the main body 30 may form various angles with the longitudinal direction of the external object 2. For example, at the second position, the longitudinal direction of the main body 30 may form an angle in a range of 0 degrees to 180 degrees with the longitudinal direction of the external object 2. In the case where the external object 2 is, for example, a temple of an eyeglass frame, at the second position, the longitudinal direction of the main body 30 may form an angle in a range of 30 degrees to 90 degrees with the longitudinal direction of the external object 2 for the user's convenience.

The first distance between the main body 30 and the plane including the side surface 11 may be larger than the second distance.

According to various embodiments of the present invention, in the case where the user uses the rotary device 1 in the state where the rotary device 1 is attached to the external object 2, the main body 30 may be made to be in contact with the user's ear or face. When the user does not use the rotary device 1, the main body 30 may be completely separated from the user's body. As the main body 30 moves in the x-axis direction as illustrated in FIG. 3, the main body 30 may be capable of moving toward or away from the external object 2.

Figure 4A:
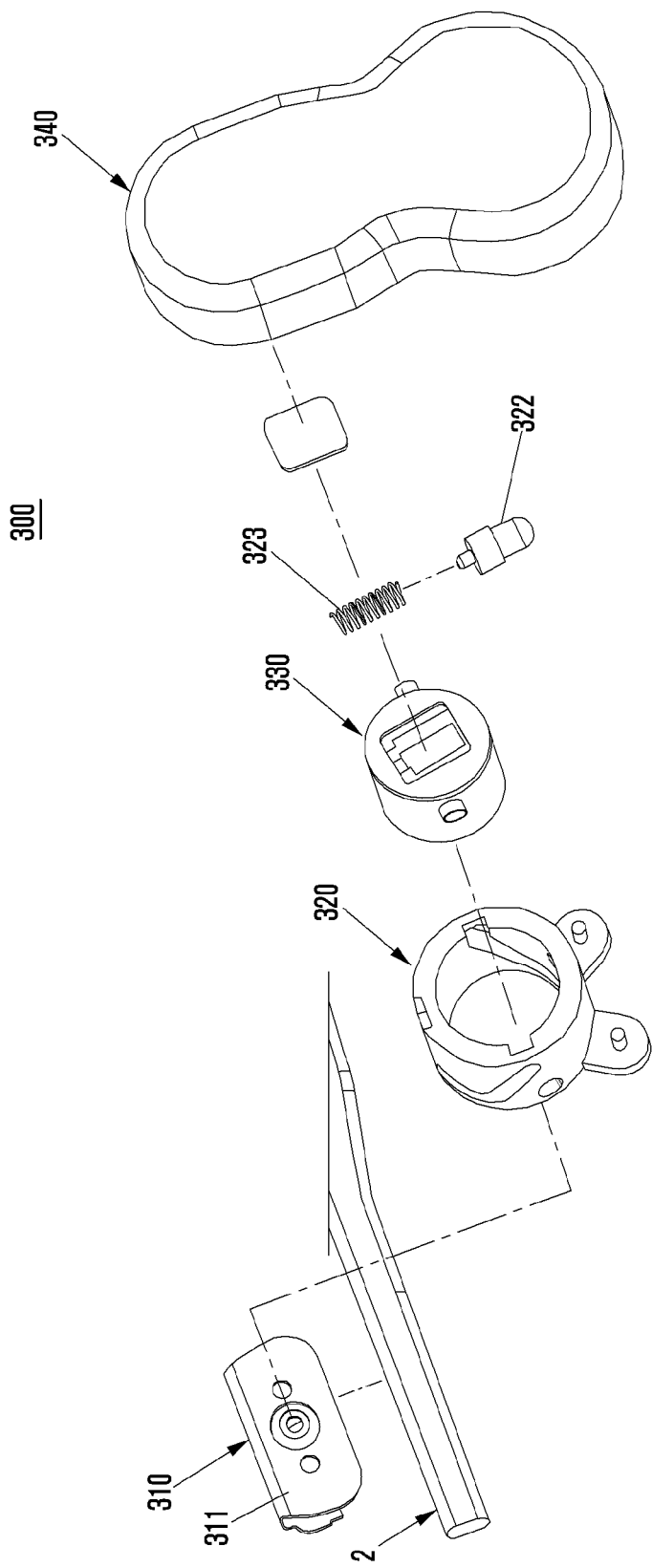
FIG. 4A and FIG. 4B are exploded perspective views of the rotary device according to an embodiment of the present disclosure.
Figure 4B:
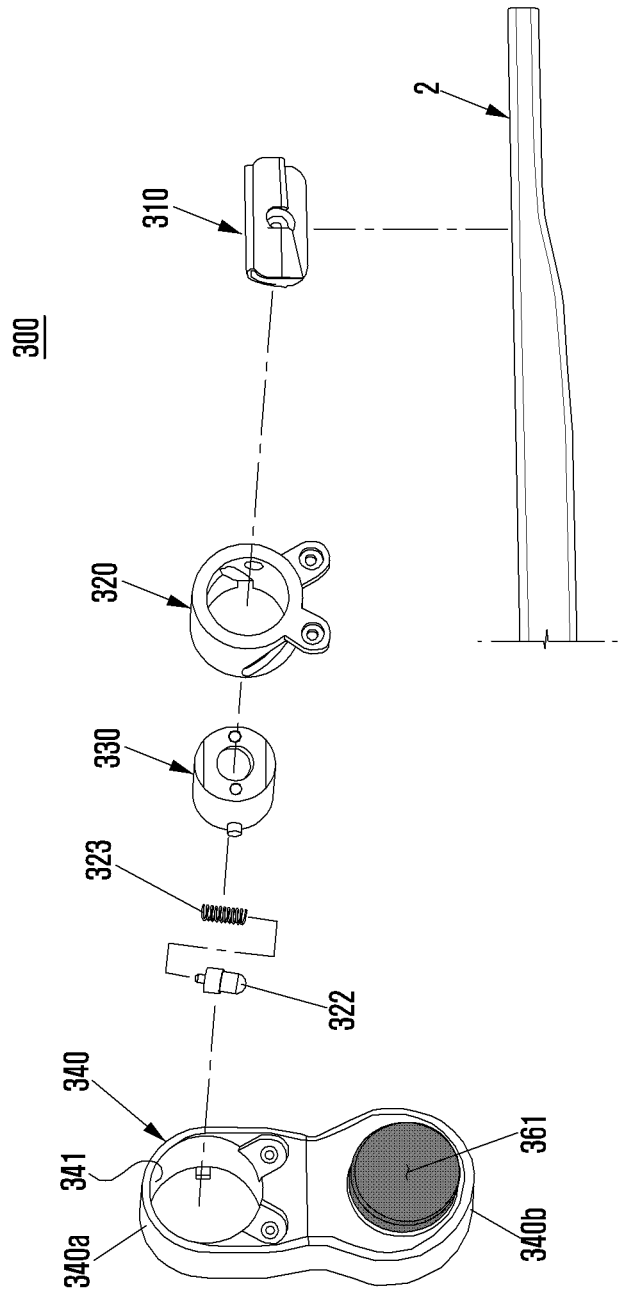

FIGS. 4A and 4B are exploded perspective views of a rotary device according to one embodiment of the present disclosure.

According to one embodiment of the present disclosure, a rotary device 300 may include a binding unit 310, an stationary unit 320, a rotary unit 330, and a main body 340.

The binding unit 310 may be coupled to an external object 2 such as a temple of an eyeglass frame. The stationary unit 320 may be connected to the binding unit 310. The rotary unit 330 may be rotatably connected to the stationary unit 320. The main body 340 may be coupled to the rotary unit 330.

According to one embodiment, the binding unit 310 may be connected or coupled to an external object, such as an eyeglass frame, through shrink fitting in a clip manner, and the rotary device 300 may be freely detachably attached to or fixed to the external object 2. The method of connecting the binding unit 310 to the external object 2 is not limited, and may be connected to the external object 2 through various methods.

The stationary unit 320 is positioned adjacent to one side surface 311 of the binding unit 310.

The stationary unit 320 is interposed between the binding unit 310 and the rotary unit 330 to allow the binding unit 310 and the rotary unit 330 to be indirectly connected with each other. The rotary unit 330 is rotatable about the stationary unit 320. The rotary device 300 may include a component or a shape to prevent the rotary unit 330 from being freely rotated about the stationary unit 320. For example, a stop pin 322 may be used for controlling the rotation range of the rotary unit 330 in relation to the stationary unit 320. When an end of the stop pin 322 penetrates the rotary unit 330 and then is inserted into the stationary unit 320, the rotation of the rotary unit 330 in relation to the stationary unit 320 may be limited. The spring 323 may provide an elastic force to allow the end of the stop pin 322 to be inserted into the stationary unit 320.

According to one embodiment, a first end 340a (an upper end in the drawing) of the main body 340 may be formed with a coupling portion 341 to be coupled to the rotary unit 330. On a second end 340b (a lower end in the drawing) of the main body 340, an additional module 361, such as a sound module, may be mounted.

Although the main body 340 is illustrated as a separate component coupled to the rotary unit 330, the main body 340 may be formed to extend from an region of the rotary unit 330. For example, the main body 340 may be formed integrally with the rotary unit 330.

A first position of the rotary unit 330 according to one embodiment of the present disclosure is described with reference to FIG. 5. A second position of the rotary unit 330 according to one embodiment of the present disclosure is described with reference to FIG. 6.

Figure 5:
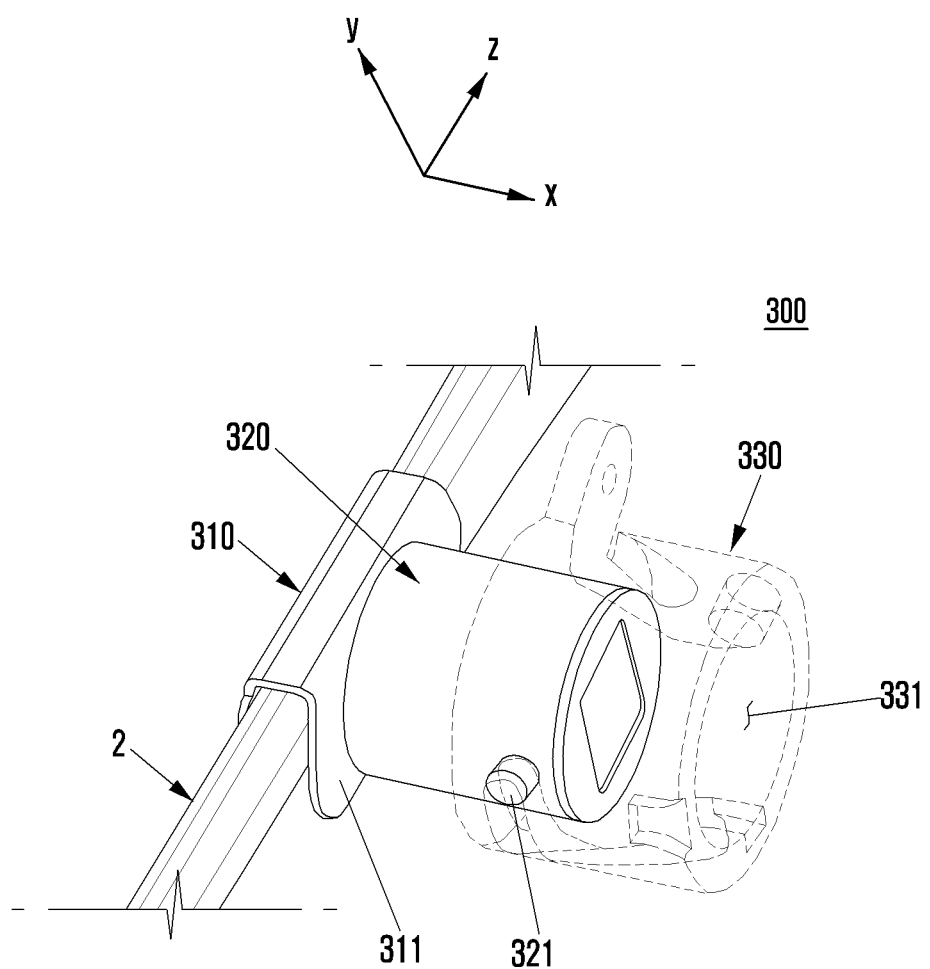
FIG. 5 is a view for describing a first position of the rotary unit according to an embodiment of the present disclosure.
Figure 6:
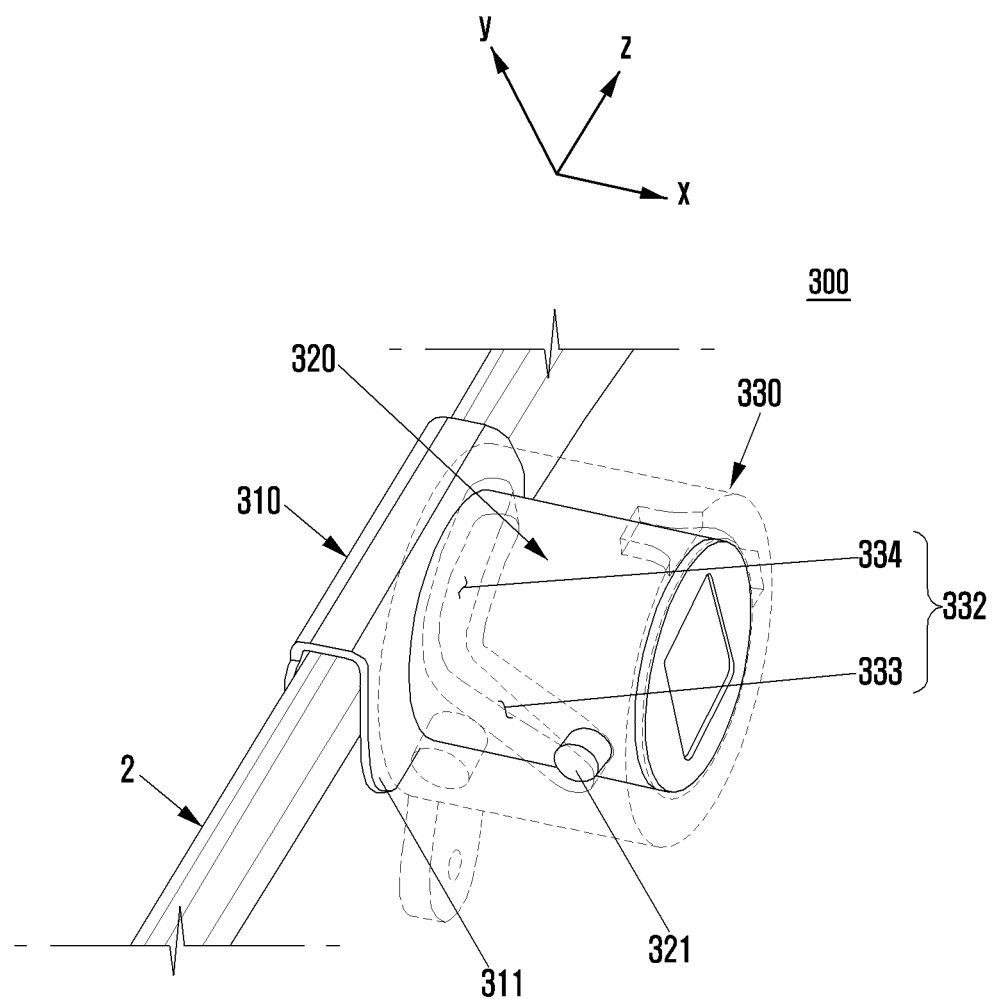
FIG. 6 is a view of the rotary unit in a second position according to an embodiment of the present disclosure.

FIGS. 5 and 6 illustrate a state where the rotary unit 330 illustrated by dotted lines is removed from the main body 340.

According to one embodiment, the rotary unit 330 may be configured to be rotatable between the first position and the second position set in relation to the stationary unit 320. The overall shape of the stationary unit 320 may be a cylindrical shape. The rotary unit 330 may have a cylinder shape that accommodates the stationary unit 320.

In the state where rotary device 300 is coupled to an external object (e.g., a temple of an eyeglass frame) 2, the first position may be a position where the main body 340 is parallel with or overlaps the external object 2. At the second position, the main body 340 may be approximately perpendicular to the external object 2. The distance of the rotary unit 330 spaced apart from the side surface of the binding unit 310 at the first position may be larger than the distance of the rotary unit 330 spaced apart from the side surface of the binding unit 310 at the second position. For example, at the second position where the main body 340 is perpendicular to the longitudinal direction of the external object 2, the main body 340 comes in close contact with the external object 2, and at the second position where the main body 340 is parallel with the longitudinal direction of the external object 2, the main body 340 is moved away from the external object 2. The user may rotate the rotary unit 330 or the main body 340 between the first position and the second position. At the second position, the additional module (e.g., sound module) mounted on the main body 340 may be in the state where it is operated. At the first position, the additional module (e.g., the sound module) may be in the state where it is not operated.

According to one embodiment, the rotary unit 330 may include an insertion part 331. The insertion part 331 refers to a region where at least a part of the stationary unit 320 is inserted. When the stationary unit 320 is inserted into the insertion part 331, the rotary unit 330 and the stationary unit 320 may be coupled with each other. A guide slot 332 may be formed on the inner circumferential surface of the insertion part 331. A guide projection 321 may be formed on the external surface of the stationary unit 320 to be movable along the guide slot 332.

When the rotary unit 330 rotates in relation to the stationary unit 320, the guide projection 321 moves along the guide slot 332, and the rotary unit 330 is movable perpendicular to the stationary unit 320. For example, since a part of the guide slot 332 is formed spirally in relation to the rotary axis direction, the guide projection 321 may be rotationally or rectilinearly moved in relation to the rotary axis of the rotary unit 330. The guide projection 321 may move while being spirally rotated, the rotary unit 330 such that is rotatable or rectilinearly movable in the rotary axis direction with respect to the stationary unit 320.

According to one embodiment, the guide slot 332 may be formed on the outer circumferential surface of the stationary unit 320. A guide projection 321 may be formed on the inner circumferential surface of the insertion part 331 to be movable along the guide slot 332, and the rotary unit 330 is rotatable with respect to the stationary unit 320.

The guide slot 332 may consist of an inclined slot 333 and a peripheral slot 334 as described later with reference to FIG. 6.

Figure 7:
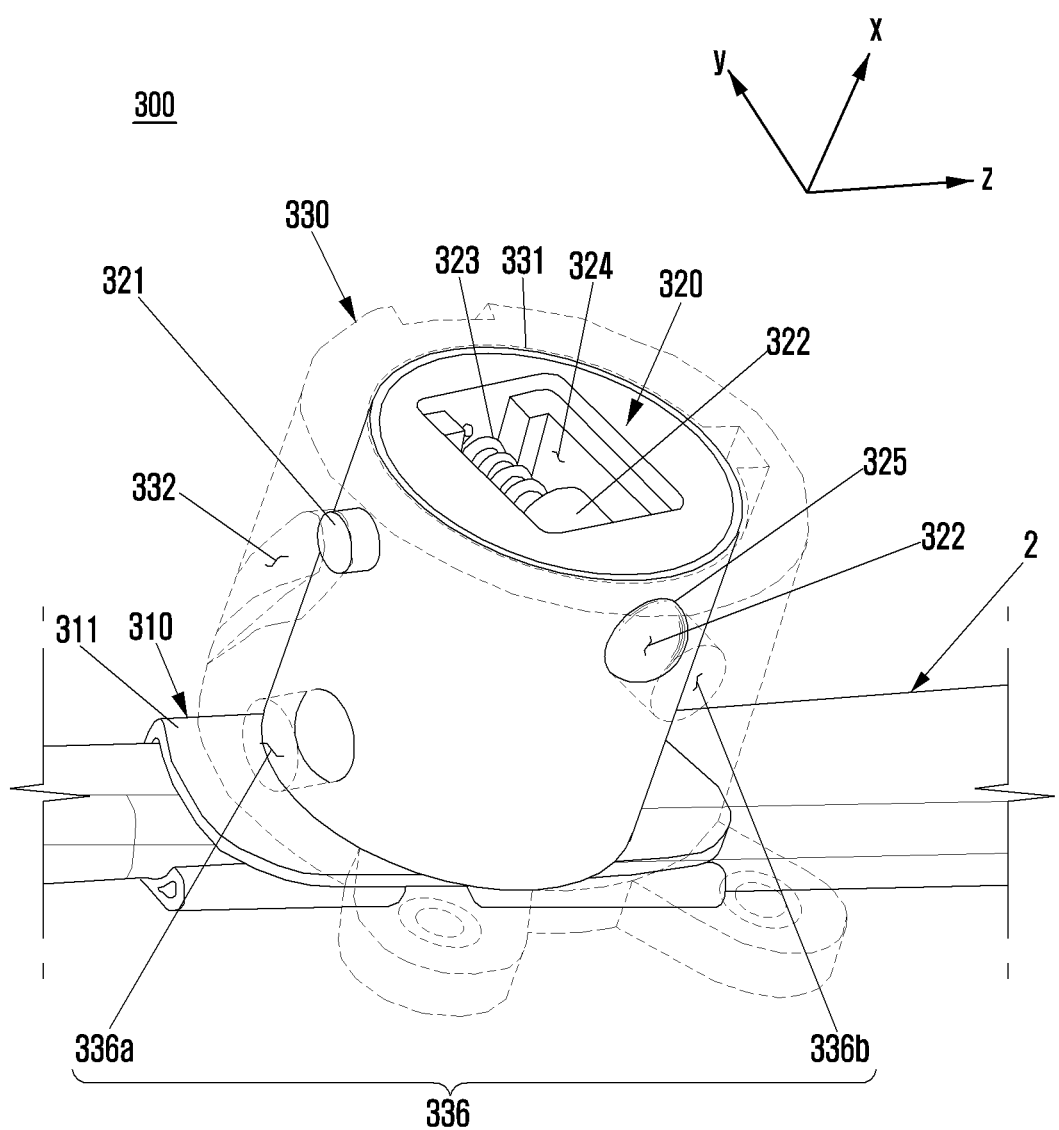
FIG. 7 is a view of a stop pin according to an embodiment of the present disclosure.

FIG. 7 is a view for describing the operation of the stop pin 322 according to one embodiment of the present disclosure.

According to various embodiments of the present disclosure, the stop pin 322 may be used so as to control the rotation range of the rotary unit 330 with respect to the stationary unit 320.

The stationary unit 320 includes a pin installation part 324. In the pin installation part 324, the stop pin 322 and a spring 323 configured to provide an elastic force to the stop 322 may be inserted and installed. In addition, the pin installation part 324 may include a through-hole 325 extending from the interior of the pin installation part 324 to the outer circumferential surface of the stationary unit 320. The stop pin 322 may be positioned to penetrate the through-hole 325, and one end of the stop pin 322 may protrude from the outer circumferential surface of the stationary unit 320.

At least one stop recess 336 may be formed on the inner circumferential surface of the insertion part 331 of the rotary unit 330. In the state where the stationary unit 320 is inserted into the rotary unit 330, one end of the stop pin 322 may be inserted into the stop recess 336. The rotation of the rotary unit 330 with respect to the stationary unit 320 may be controlled or limited, for example, by the interaction of the stop pin 322 and the stop recess 336.

In order to ensure that the stop pin 322 is easily separated from the stop recess 336, the one end of the stop pin 322 inserted into the stop recess 336 may be formed in a hemispherical shape. In the state where the one end of the stop pin 322 is inserted into the stop recess 336, the rotation of the main body 340 with respect to the stationary unit 320 may be limited, but when the user applies a force to the main body 340 to rotate the main body 340, the one end of the stop pin 322 may be released from the stop recess 336. When the rotary unit 330 is rotated, the stop pin 322 may be introduced into the stationary unit 320, and the one end of the stop pin 322 may come in contact with the inner circumferential surface of the rotary unit 330. For example, when the main body 340 is at the first position, the one end of the stop pin 322 may be positioned in the first stop recess 336*a*. When the main body 340 started to rotate from the first position, the one end of the stop pin 322 may be slid while being in contact with the inner circumferential surface of the rotary unit 330 during the rotation. When the rotary unit 330 is located at the second position, the one end of the stop pin 322 may be inserted into the second stop recess 336*b* by the elastic force provided by the spring 323. At the second position, the rotation of the rotary unit 330 with respect to the stationary unit 320 may also be controlled or limited.

According to one embodiment, two or more stop recesses 336 may be formed on the inner circumferential surface of the rotary unit 330.

Referring to FIG. 6, a part of the guide slot 332 may be formed to be inclined. According to one embodiment, the guide slot 332 may consist of an inclined slot 333 and a peripheral slot 334. The inclined slot 333 may be formed on the inner circumferential surface of the insertion part 331 to be inclined. The peripheral slot 334 may be formed to extend from the inclined slot 333, and formed along the periphery of the inner circumferential surface of the insertion part 331.

When the guide projection 321 moves along the inclined slot 333, the rotary unit 330 is moved toward or away from the side surface of the binding unit 310. For example, when the guide projection 321 moves along the inclined slot 333, the main body 340 may be moved toward or away from the external object 2, such as an eyeglass frame. When the guide projection 321 is moved along the inclined slot 333, the additional module (e.g., a sound module) mounted on the main body 340 may be moved toward or away from the user's face.

Figure 8A:
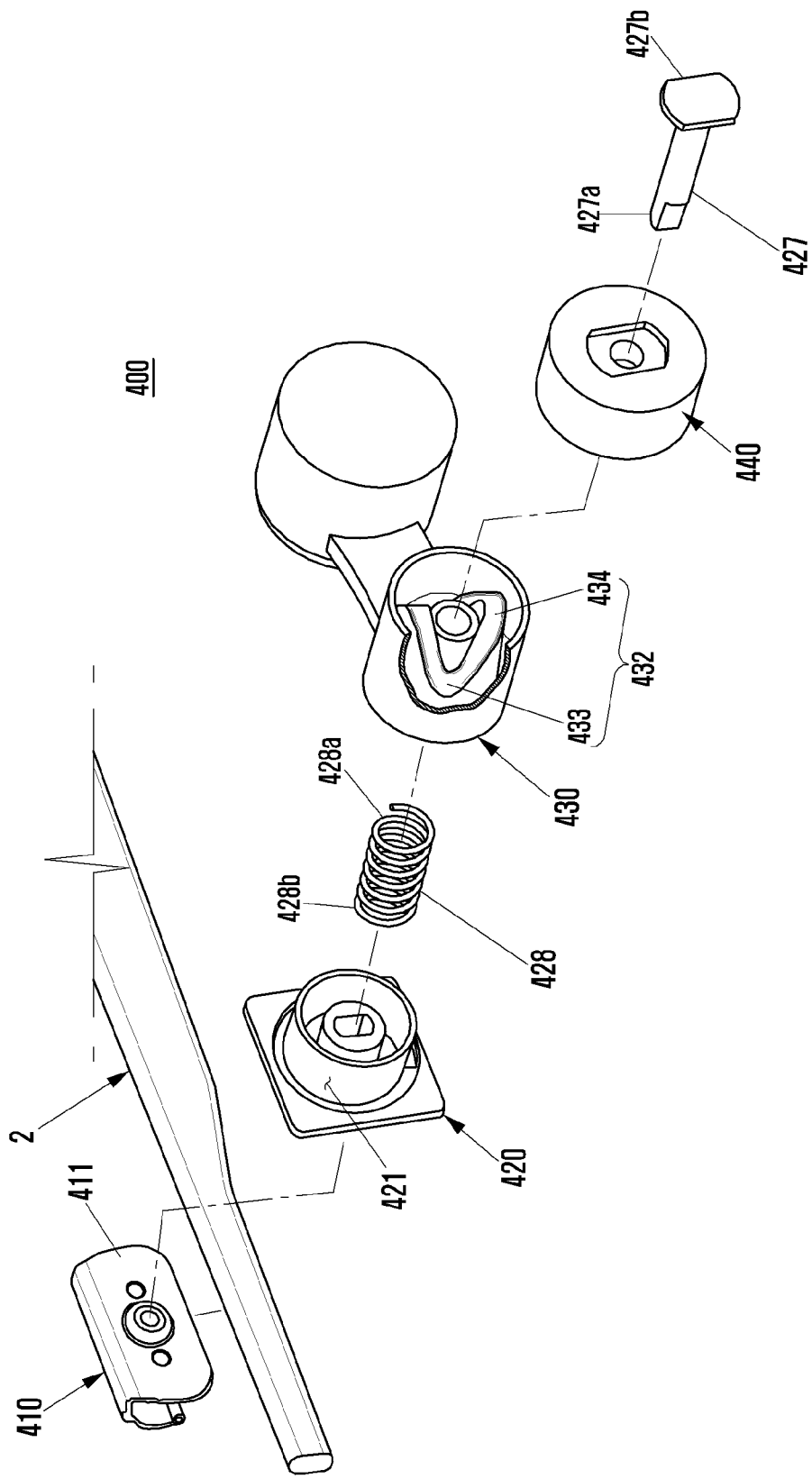
FIG. 8A and FIG. 8B are exploded perspective views of a rotary device according to an embodiment of the present disclosure.
Figure 8B:
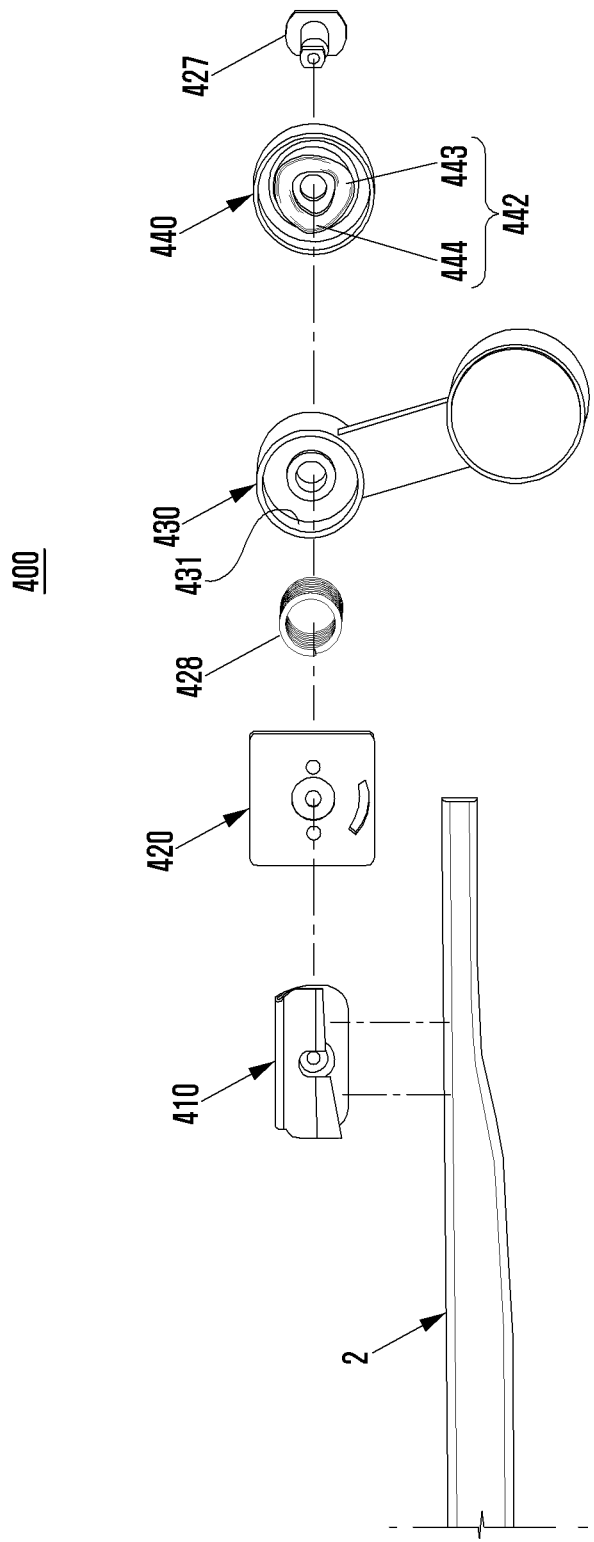
Figure 9:
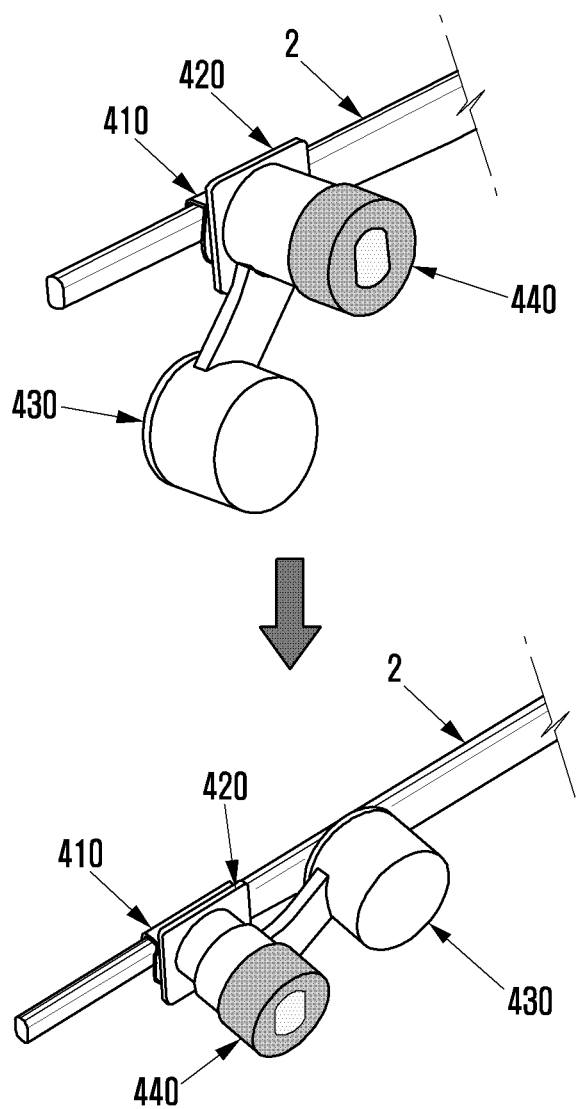
FIG. 9 is a view illustrating an operation state of the rotary device according to an embodiment of the present disclosure.
Figure 10:
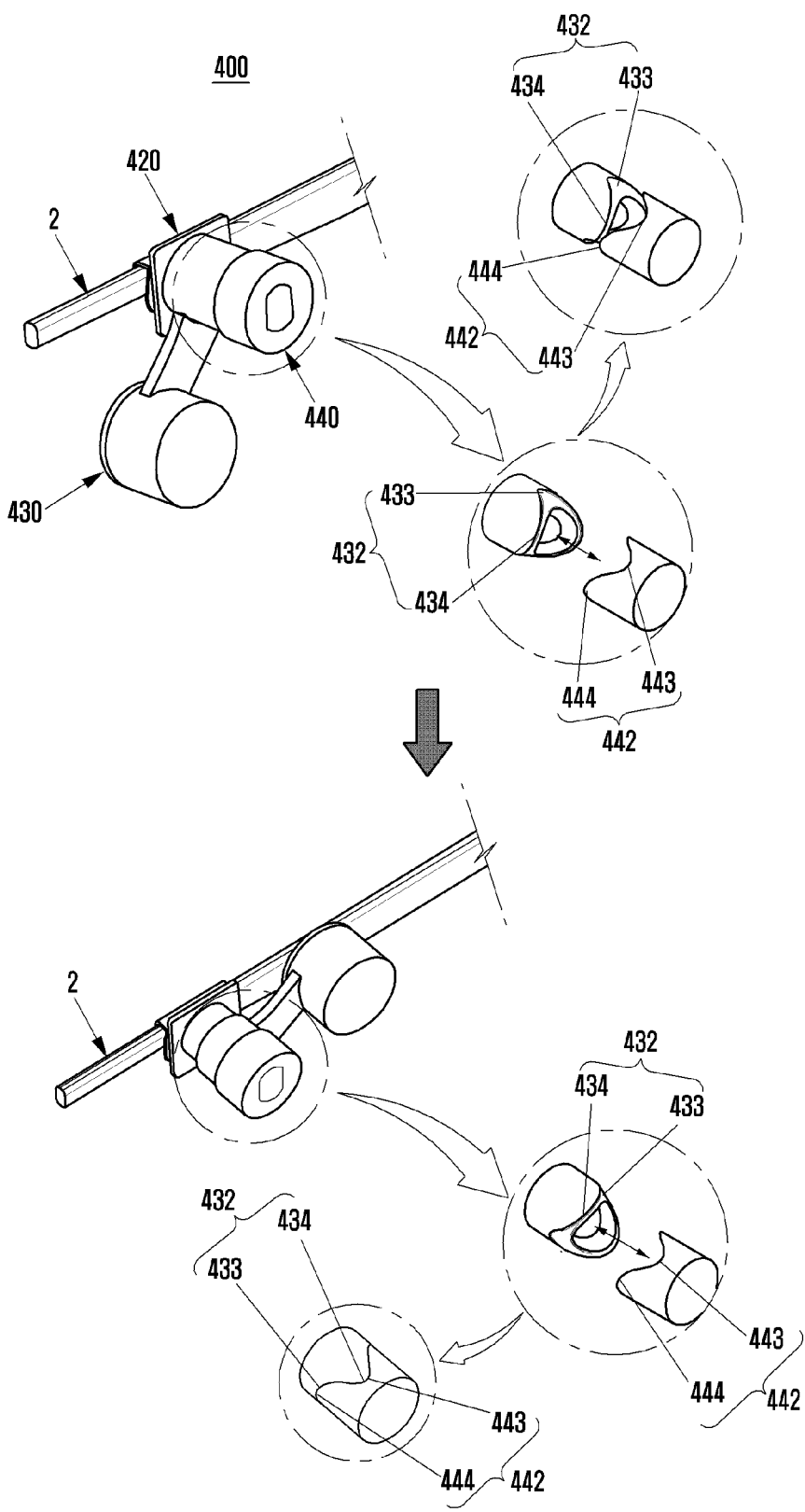
FIG. 10 is a view for describing an operation state of a guide cam and a rotary cam according to an embodiment of the present disclosure.

FIGS. 8A and 8B are exploded perspective views illustrating a rotary device 400 according to one embodiment of the present disclosure, FIG. 9 is a view illustrating an operation state of the rotary device, and FIG. 10 is a view for describing an operation state of a guide cam and a rotary cam of the rotary device 400 of FIG. 8.

According to one embodiment of the present disclosure, the rotary device 400 may include a binding unit 410, a stationary unit 420, a main body 430, and/or a guide body 440.

The binding unit 410 may be coupled to an external object 2, such as an eyeglass frame. The stationary unit 420 may be connected to the binding unit 410. The main body 430 may include a rotary unit rotatably connected to the stationary unit 420 on one side, and an additional module 461 (see FIG. 11) on the other side. The guide body 440 may be coupled to a rotary unit of the main body 430.

Referring to FIGS. 9 and 10, the main body 430 may be connected or coupled to be rotatable between a first position and a second position set with respect to the stationary unit 420. For example, at the first position where the rotary device 400 is coupled to the external object 2, such as a temple, the rotary unit 330 (see FIGS. 4 to 7) of the main body 430 may be parallel with the longitudinal direction of the external object 2. At the second position, the rotary unit of the main body 430 may be approximately perpendicular to the longitudinal direction of the external object 2.

The distance of the rotary unit of the main body 430 spaced apart from a side surface of the binding unit 410 at the first position may be larger than the distance of the rotary unit of the main body 430 from the side surface of the binding unit 410 at the second position.

According to one embodiment, the guide body 440 is positioned to be in contact with the rotary unit of the main body 430 in the region opposite to the region where the stationary unit 420 and the rotary unit of the main body 430 are coupled to each other. The guide body 440 may guide the rotary unit of the main body 430 to be moved toward or away from the binding unit 410.

According to one embodiment of the present disclosure, the rotary device 400 may further include a cam shaft 427 that forms a rotary axis of the rotary unit of the main body 430.

The cam shaft 427 may be installed through the rotary unit of the main body 430. One end 427a of the cam shaft 427 may be coupled to the stationary unit 420, and the other end 427b may be fixedly connected to the guide body 440.

Referring to FIG. 10, the guide body 440 may guide the main body 430. The rotary unit of the main body 430 may include a rotary cam 432. The rotary cam 432 may include a concave cam recess 433 and a convex cam projection 434. The guide body 440 may include a guide cam 442 corresponding to the rotary cam 432 of the rotary unit of the main body 430. The guide cam 442 may include a concave cam recess 443 and a convex cam projection 444.

The rotary cam 432 and the guide cam 442 may engage with each other. For example, the rotary cam 432 and the guide cam 442 may be rotatable about the same axis in the state where they are engaged with each other.

As the rotary cam 432 rotates with respect to the guide cam 442, the cam projection 434 of the rotary cam 432 may move in a sliding manner between the cam recess 443 and the cam projection 444 of the guide cam 442. According to one embodiment, when the main body 430 is located at the first position, the cam projection 434 of the rotary cam 432 may be positioned adjacent to the cam recess 443 of the guide cam 442 between the cam recess 443 of the guide cam 442 and the cam projection 444 of the guide cam 442. When the main body 430 is located at the second position, the cam projection 434 of the rotary cam 432 may be positioned adjacent to the cam projection 444 of the guide cam 442 between the cam recess 443 of the guide cam 442 and the cam projection 444 of the guide cam 442. When the main body 430 is located at the first position, the cam projection 444 of the guide cam 442 and the cam recess 433 of the rotary cam 432 may be engaged with each other. At the first position, the main body 430 may be spaced apart from the binding unit 410 or the external object 2 at a maximum or full extent or distance.

According to one embodiment, when a cylinder part 421 formed in the stationary unit 420 may be inserted into the insertion part 431 of the rotary unit of the main body 430. A spring 428 may be provided between the stationary unit 420 and the rotary unit of the main body 430. One end 428b of the spring 428 may be inserted into the cylinder part 421 of the stationary unit 420, and the other end 428a of the spring 428 may be inserted into the insertion part 431 of the rotary unit of the main body 430. The spring 428 may provide an elastic force to the main body 430 and the stationary unit 420. In addition, the spring 428 may provide an elastic or a biasing force that causes the main body 430 to be biased away from the stationary unit 420.

At the second position, the main body 430 may be perpendicular to a temple as the external object 2, in which state the cam projection 444 of the guide cam 442 and one end of the cam projection 434 of the rotary cam 432 come in contact with each other. At this time, since the spring 428 pushes the rotary unit of the main body 430 toward the guide body 440, a restoration force is generated to cause the cam projection 434 of the rotary cam 432 to move to the cam recess 443 of the guide cam 442. In order to prevent this, the angle between the first position and the second position may exceed 90 degrees.

In the case where the angle between the first position and the second position is 90 degrees, the main body 430 may approach the external object 2 to maximum. Thus, the angle between the first position and the second position may be similar to 90 degrees.

In order to prevent the reverse rotation of the main body 430, and allow the main body 430 to properly approach the binding unit 410, the angle between the first position and the second position may exceed 90 degrees.

According to one embodiment, the stationary unit 420 may guide the main body 430.

Although not specifically illustrated, for example, the guide cam 442 corresponding to the rotary cam 432 of the rotary unit of the main body 430 may be included in the stationary unit 420, the guide body 440 may include the cylinder part 421, and the spring 428 may be provided between the guide body 440 and the rotary unit of the main body 430.

Figure 11:
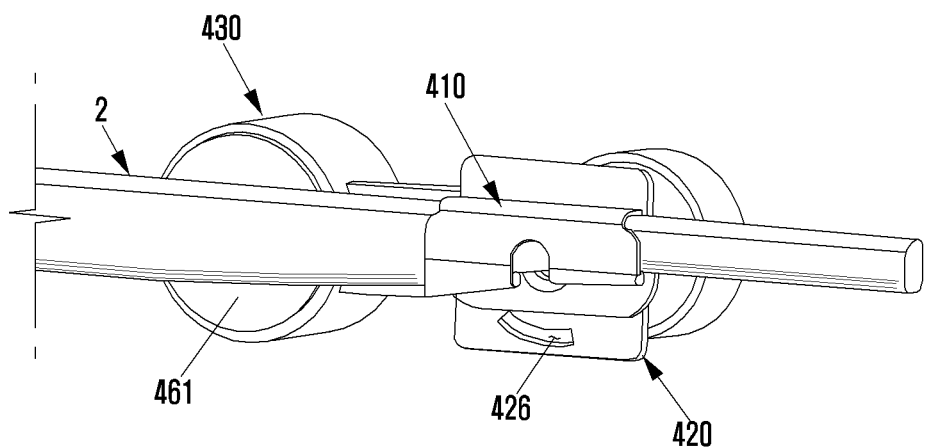
FIG. 11 is a view for describing a stop recess according to an embodiment of the present disclosure.
Figure 11:
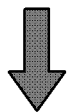
Figure 11:
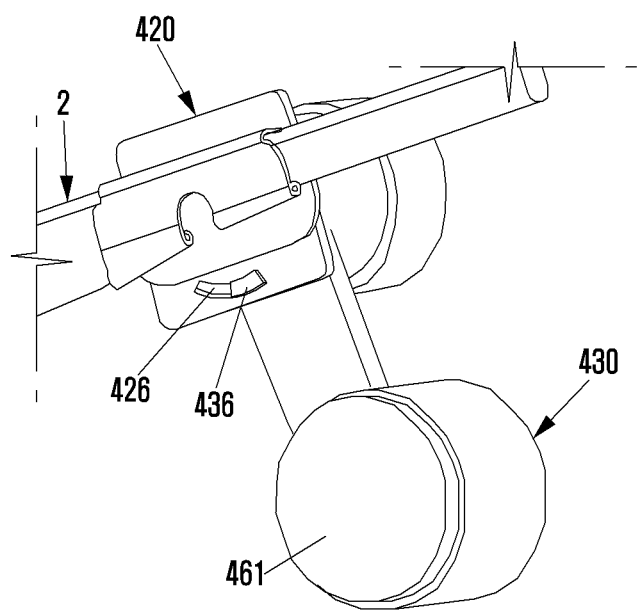

FIG. 11 is a view for describing a stop recess 426 according to one embodiment of the present disclosure.

The stationary unit 420 may further include the stop recess 426. The second position of the main body 430 may be determined by the position of the stop recess 426. The main body 430 may include a stop projection 436 that catches or engages the stop recess 426 at the second position. When the stop projection 436 is caught or engages with the stop recess 426, the main body 430 is inhibited or prevented from rotating in the direction opposite to the direction directed from the second position to the first position.

Figure 12:
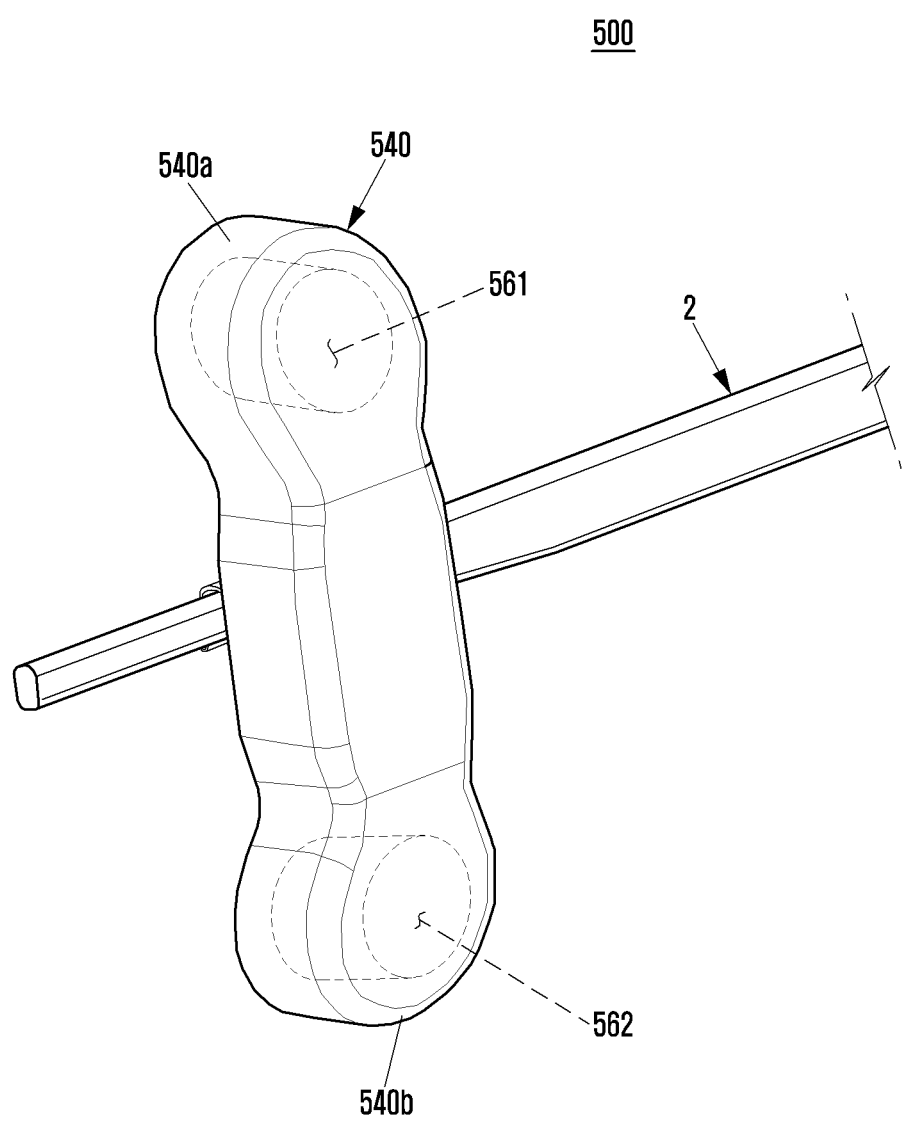
FIG. 12 is a perspective view of a rotary device according to an embodiment of the present disclosure.

FIG. 12 is a perspective view illustrating a rotary device 500 according to one embodiment of the present disclosure.

According to one embodiment of the present disclosure, the rotary device 500 may include two or more additional modules (e.g., a sound module and various sensors) mounted thereon.

The rotary device 500 may include a binding unit capable of being coupled to an external object 2, an stationary unit connected to the binding unit, and a rotary unit connected to be rotatable about one axis between a plurality of positions set with respect to the stationary unit. As the rotary unit is rotated with respect to the stationary unit, the rotary unit may sequentially move toward or away from one side surface of the binding unit at the plurality of positions. The rotary device 500 may include a main body 540 coupled to the rotary unit.

A first additional module 561 and a second additional module 562 may be mounted on one end 540a and on the other end 540b of the main body 540, respectively. At the first position, the rotary unit may be moved away from the external object, in which case the main body 540 may be positioned to be parallel with the external object. As being rotated from the first position, the main body 540 may be spaced apart from the external object 2 or come in close contact with the external object 2, in which the spacing and close contact may be sequentially performed.

The first additional module 561 and the second additional module 562 may be configured to be operated when they are located at a set operation position among a plurality of positions. A position where the first additional module 561 is parallel with the longitudinal direction of the external object 2 may be referred to as a first position, and a position rotated 90 degrees from the first position may be referred to as a second position. A position rotated 90 degrees from the second position may be referred to as a third position. The first position and the third position may form an angle of 180 degrees therebetween. A position rotated 90 degrees from the third position may be referred to as a fourth position. The second position and the fourth position may form an angle of 180 degrees therebetween. Alternatively, a plurality of positions may be defined as five or more positions. The main body 540 may include at least two additional modules. For example, the main body 540 may include two different sensor kinds, and the kind of sensor coming in contact with the user's face may be changed as the main body 540 is rotated. For example, when an HRM sensor is mounted as the first additional module 561 and a sound module is mounted as the second additional module 562, the HRM sensor and the sound module may be caused to selectively come in contact with the user's face as the main body 540 is rotated.

At the first position, the main body is parallel with the longitudinal direction of a temple as the external object 2, and at the second position, the first module 561 or the second module 562 is approximately perpendicular to the longitudinal direction of the temple as the external object 2. The user may rotate the main body 540 by a set unit (e.g., a 90 degree unit), and the first additional module 561 and the second additional module 562 may be adjusted to come selectively close contact with the user's face.

According to one embodiment, it is possible to adjust the operation of the first additional module 561 or the second additional module 562 to be operated as the main body 540 is rotated. When the sound module or the HRM sensor is in close contact with the user's face at the second position or the fourth position, an adjustment may be made so that the sound module or the HRM sensor is operated. The operation of the sound module or the HRM sensor may be stopped at the first position or the third position. A camera may be additionally mounted on the main body 540, and the camera may be directed in the user's visual line at the first position. For example, at the first position, the camera may photograph in the same direction as the user's visual line.

In the prior art, in order to use a camera, a sound device, or a HRM sensor, it was necessary for the user to use each of separately provided devices. According to the rotary device of the present disclosure, it is now possible to conveniently carry the devices without the necessity of providing respective devices separately, and each function can be selected through a simple rotating operation.

Figure 13:
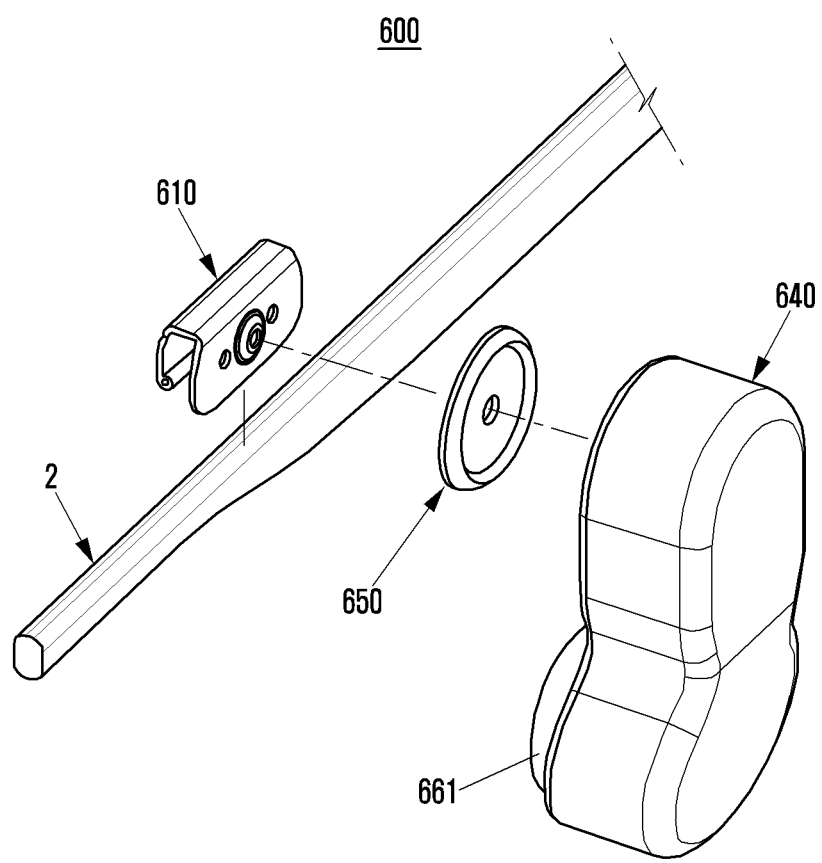
FIG. 13 is an exploded perspective view of a rotary device according to an embodiment of the present disclosure.

FIG. 13 is a perspective view of a rotary device 600 according to one embodiment of the present disclosure.

Since the skeletal muscles of faces of persons are different from each other, the position of a sound device should be adjustable according to the shape of the user's face. For example, in the case where the sound module 661 is a bone conduction speaker, the position of the sound module 661 should be adjustable to be correctly in contact with a specific position of the user's face. The position of the binding unit 610 to be coupled to the external object 2 may be changed. However, only with the coupling position of the binding unit 610, it is difficult to correctly determine the position where the bone conduction speaker is in contact with the user's face.

The rotary device 600 may be further provided with a rotary member 650 to adjust the rotation angle between the binding unit 610 and the main body 640.

Figure 14:
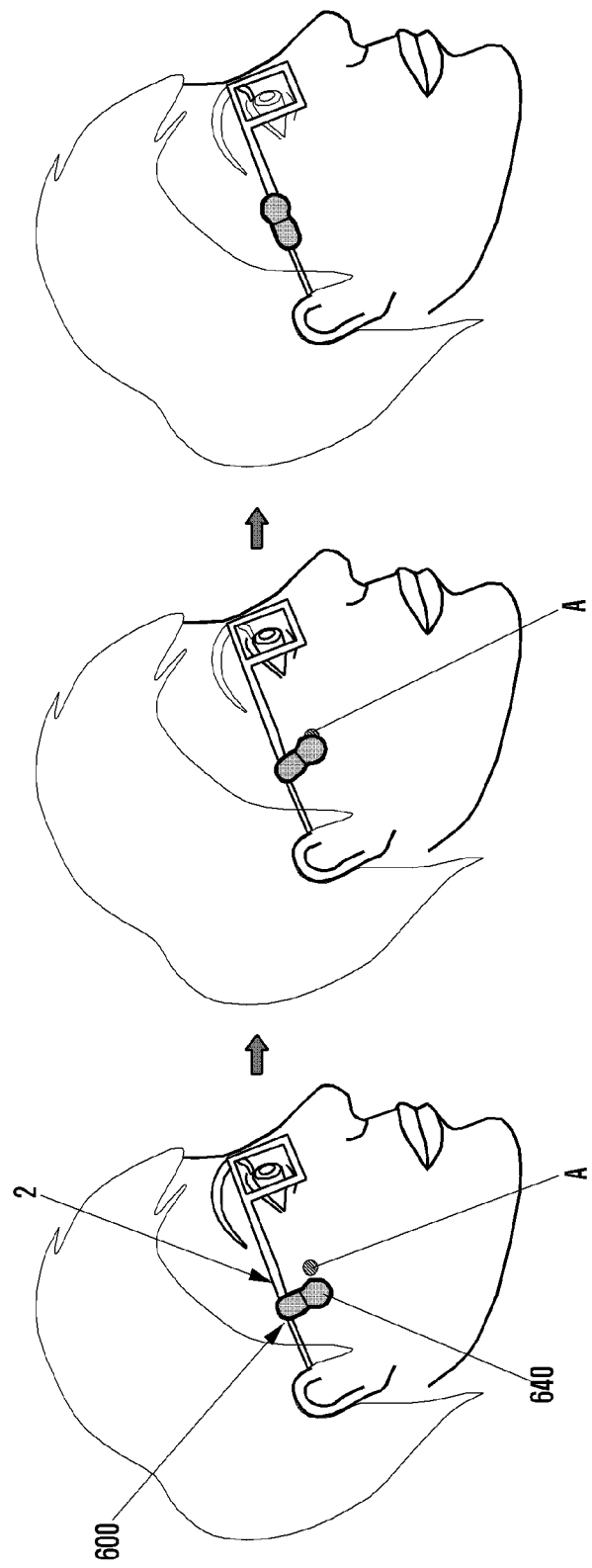
FIG. 14 is a view illustrating a use state of a rotary device according to an embodiment of the present disclosure.

FIG. 14 is a view illustrating a use state of the rotary device 600 according to one embodiment of the present disclosure.

The relative angle between the temple as the external object 2 and the main body 640 may be adjusted through the rotation of the rotary member 650. Although not illustrated, according to one embodiment, the rotary device 600 may include a stationary unit. The stationary unit may be configured to have the same constitution as those of the above-described embodiments. The rotary member 650 may be positioned between the binding unit 610 and the stationary unit, and may be capable of adjusting the angle between the binding unit 610 and the stationary unit. For example, the operation position of the sound module 661 (or the second position) may be set as the initial position A through the rotary member 650. Through this, the operation position of the sound module may be adjusted to be suitable for the shape of the user's face.

Figure 15:
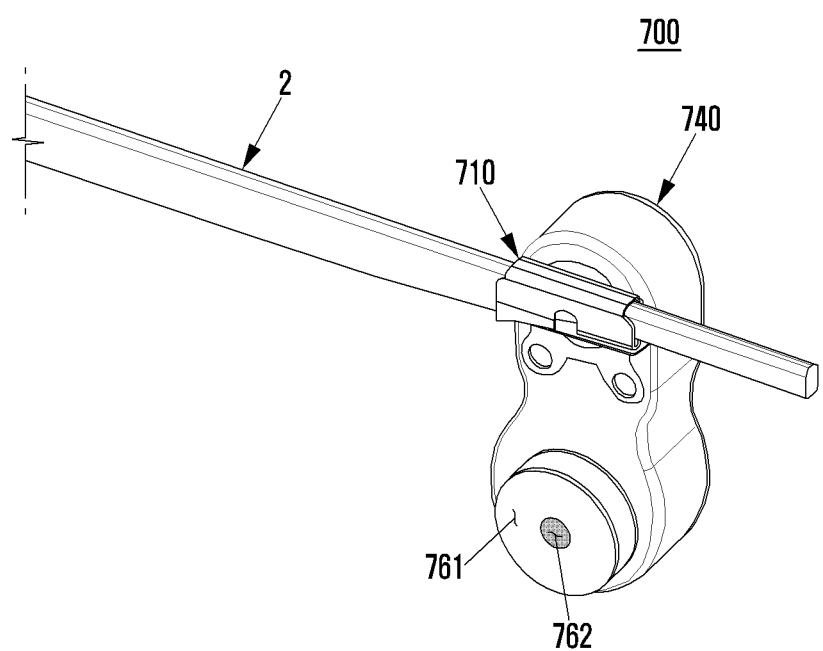
FIG. 15 is a perspective view of a rotary device according to an embodiment of the present disclosure shown coupled to an object.

FIG. 15 is a perspective view of a rotary device 700 according to one embodiment of the present disclosure.

As in FIG. 13, the position where the binding unit 710 is coupled to an external object 2 can be changed.

Within a main body 740, not only an additional module, such as a sound module 761, a sensor 762, such as a touch sensor or a proximity sensor, may be additionally included. That is, through the sensor 762, it may be recognized that the sound module 761 of the main body 740 is contact with the user's skin, and the second position or the operation position of the sound module 761 may be sensed.

According to one embodiment, it is possible to sense, through the sensor 762, that the additional module is not in contact with the user's skin and to stop the operation of the sound module 761 or to turn off the power of the sound module 761. On the contrary, when it is recognized, through the sensor 762, that the additional module is in contact with the user's skin, the power of the sound module 761 may be turned on.

The rotation of the rotary device 700 may be sensed not only through the sensor 762, but also through a separate physical switch, and the management of power through this may be enabled not only through the rotary device 700, but also through a main device which may be connected with the rotary device 700.

According to one embodiment, the operation of the rotary device may be controlled through an operation of a switch or an application of the main device. Alternatively, the application operated in the main device may be controlled through the operation of the rotary device 700. For example, when the main body 740 of the rotary device 700 is positioned at the first position during listening to music through an application executed in the main device, the operation of the application reproducing the music may be terminated.

Figure 16:
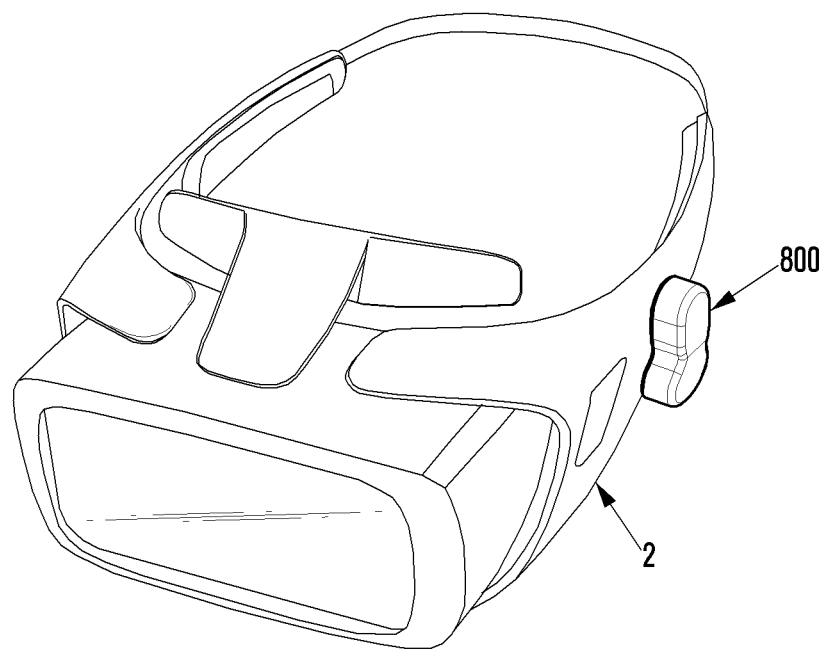
FIG. 16 and FIG. 17 are views illustrating examples of utilizing rotary devices of the present disclosure.
Figure 17:
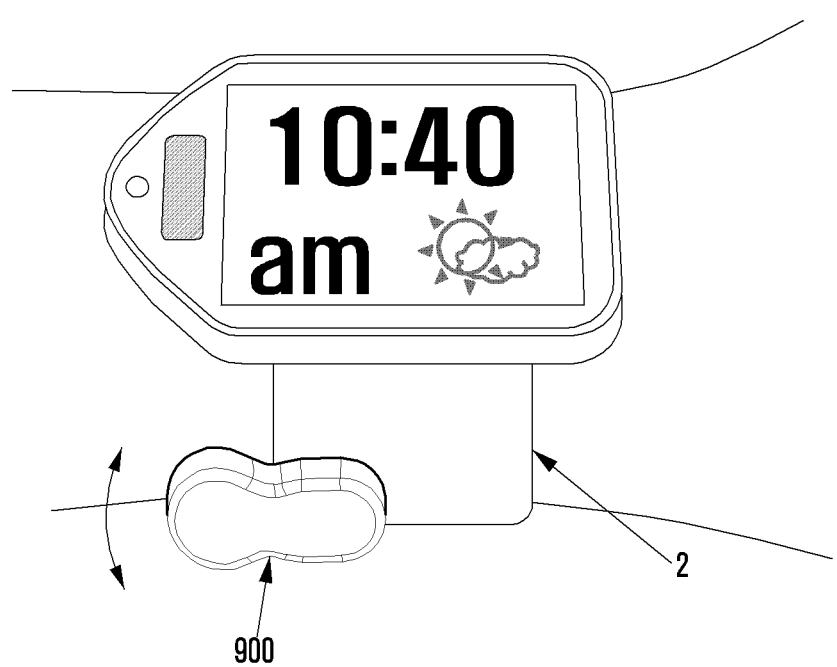

FIGS. 16 and 17 are views illustrating examples of utilizing rotary devices 800 and 900 of the present invention.

Although descriptions have been made on the cases in which the rotary device 1 is mounted on a temple of an eyeglass as an external object 2, the rotary device 1 may be fabricated in various sizes and shapes and may be mounted on various wearable devices.

According to various embodiments, FIG. 16 illustrates a case in which the rotary device 800 is mounted on an external object 2, such as a wearing member of an HMD. FIG. 17 illustrates a case in which the rotary device 900 is applied to an external object 2, such as a band of a watch type wearable device. For example, an additional module may be equipped with a sensor capable of measuring a body function, such as an HRM sensor or a vein sensor.

According to various embodiments of the present invention, a rotary device is capable of being in close contact with the user's body when it is used, and thus, the usability of the rotary device can be enhanced. In addition, when the rotary device is not used, the user may move in the state where the rotary device is fixed to, for example, eyeglasses without necessity of separately carrying it, the portability of the rotary device can be enhanced.

While this disclosure has been particularly shown and described with reference to particular embodiments thereof, it will be understood by those skilled in the art that various changes in form and details may be made therein without departing from the spirit and scope of this disclosure as defined by the appended claims.

What is claimed is:

1. A rotary device comprising: a binding unit detachably coupled to a part of an external object and including a side surface defining a geometric plane and having a length through which a longitudinal axis extends; a stationary unit positioned adjacent to the side surface of the binding unit and formed integrally with or coupled to the binding unit; a rotary unit coupled to the stationary unit, the rotary unit including a first end and a second end, the first and second ends being opposite one another, the first end being rotatably coupled to the stationary unit; and wherein the rotary unit is rotatable between a first position where the rotary unit forms a first angle with respect to the longitudinal axis and a second position where the rotary unit forms a second angle with the respect to the longitudinal axis, wherein at the first position, the second end of the rotary unit is at a first distance from the geometric plane, and at the second position, the second end of the rotary unit is at a second distance from the geometric plane, the second distance being different from the first distance, wherein the stationary unit includes: a stop pin and a pin installation part, the pin being inserted into the pin installation part, and further comprising a spring configured to provide an elastic force to the stop pin, and wherein a through hole is formed in the pin installation part to extend to an outer circumferential surface of the stationary unit, the stop pin being positioned through the through hole an one end of the stop pin protruding from the outer circumferential surface of the stationary unit.

2. The rotary device of claim 1, further comprising:
a main body fixed to the rotary unit, wherein the main body includes an electronic part.

3. The rotary device of claim 2, wherein the main body has a longitudinal axis extending therethrough, and wherein at the first position the longitudinal axis of the main body is substantially parallel to the longitudinal axis of the external object.

4. The rotary device of claim 2, wherein, at the second position, a longitudinal direction of the main body forms an angle within a range of 0 to 180 degrees inclusive with respect to the longitudinal axis of the external object.

5. The rotary device of claim 2, wherein the main body is connected to the rotary unit at the first end and includes the electronic part at the second end.

6. The rotary device of claim 2, wherein the electronic part includes a bone conduction speaker.

7. The rotary device of claim 1, wherein the rotary unit includes an insertion part, into which at least a part of the stationary unit is inserted,
the insertion part includes a guide slot formed on an inner circumferential surface,
the stationary unit includes a guide projection formed on an outer circumferential surface, and
when the rotary unit is rotated with respect to the stationary unit, the guide projection is moved along the guide slot to guide a vertical movement of the rotary unit with respect to the stationary unit.

8. The rotary device of claim 2, wherein the main body further includes a touch sensor configured to control an on/off operation of the electronic part.

9. The rotary device of claim 1, further comprising: a rotary member configured to adjust a rotation angle between the binding unit and the stationary unit.

10. A rotary device comprising:
a binding unit detachably coupled to a part of an external object and including a side surface defining a geometric plane an having a length through which a longitudinal axis extends;
a stationary unit positioned adjacent to the side surface of the binding unit and formed integrally with or coupled to the binding unit;
a rotary unit coupled to the stationary unit, the rotary unit including a first end and a second end, the first and second ends being opposite one another, the first end being rotatably coupled to the stationary unit;
wherein the rotary unit is rotatable between a first position where the rotary unit forms a first angle with respect to the longitudinal axis and a second position where the rotary unit forms a second angle with respect to the longitudinal axis,
wherein at the first position, the second end of the rotary unit is a first distance form the geometric plane, and at the second position, the second end of the rotary unit is a second distance from the geometric plane, the second distance being different from the first distance,
wherein the rotary unit includes an insertion part, into which at least a part of the stationary unit is inserted, the insertion part includes a guide slot formed on an inner circumferential surface, the stationary unit includes a guide projection formed on an outer circumferential surface, and when the rotary unit is rotated with respect to the stationary unit, the guide projection is move along the guide slot to guide a vertical movement of the rotary unit with respect to the stationary unit,
wherein the stationary unit includes: a stop pin and a pin installation part, the pin being inserted into the pin installation part, and further comprising a spring configured to provide an elastic force to the stop pin, and
wherein a through hole is formed in the pin installation part to extend to the outer circumferential surface of the stationary unit, the stop pin being positioned through the through hole and one end of the stop pin protruding from the outer circumferential surface of the stationary unit.

11. The rotary device of claim 10, wherein a stop recess is formed on the inner circumferential surface of the insertion part, and when one end of the stop pin is inserted into the stop recess, the rotation of the rotary unit with respect to the stationary unit is limited by a length of the stop recess.

12. The rotary device of claim 11, wherein the stop recess includes a first stop recess and a second stop recess, and when the rotary unit is located at the first position, the one end of the stop pin is inserted into the first stop recess, and when the rotary unit is located at the second position, the one end of the stop pin is inserted into the second stop recess.

13. A rotary device comprising:
a binding unit detachably coupled to a part of an external object and including a side surface defining a geometric plane an having a length through which a longitudinal axis extends;
a stationary unit positioned adjacent to the side surface of the binding unit and formed integrally with or coupled to the binding unit; and
a rotary unit coupled to the stationary unit, the rotary unit including a first end and a second end, the first and second ends being opposite one another, the first end being rotatably coupled to the stationary unit,
wherein the rotary unit is rotatable between a first position where the rotary unit forms a first angle with respect to the longitudinal axis and a second position where the rotary unit forms a second angle with respect to the longitudinal axis,
wherein at the first position, the second end of the rotary unit is a first distance form the geometric plane, and at the second position, the second end of the rotary unit is a second distance from the geometric plane, the second distance being different from the first distance,
wherein the rotary unit includes an insertion part, into which at least a part of the stationary unit is inserted, the insertion part includes a guide slot formed on an inner circumferential surface, the stationary unit includes a guide projection formed on an outer circumferential surface, and when the rotary unit is rotated with respect to the stationary unit, the guide projection is move along the guide slot to guide a vertical movement of the rotary unit with respect to the stationary unit;
wherein the guide slot further includes: an inclined slot that is inclined on the inner circumferential surface of the insertion part; and a peripheral slot extending from the inclined slot to the inner circumferential surface of the insertion part, and
wherein when the guide projection is moved along the inclined slot, the stationary unit is correspondingly moved toward or away from the binding unit depending on a direction the guide projection is moved along the inclined slot.

14. A rotary device comprising:
a binding unit detachably coupled to a part of an external object and including a side surface defining a geometric plane an having a length through which a longitudinal axis extends;
a stationary unit positioned adjacent to the side surface of the binding unit and formed integrally with or coupled to the binding unit;
a rotary unit coupled to the stationary unit, the rotary unit including a first end and a second end, the first and second ends being opposite one another, the first end being rotatably coupled to the stationary unit,
wherein the rotary unit is rotatable between a first position where the rotary unit forms a first angle with respect to the longitudinal axis and a second position where the rotary unit forms a second angle with respect to the longitudinal axis,
wherein at the first position, the second end of the rotary unit is a first distance form the geometric plane, and at the second position, the second end of the rotary unit is a second distance from the geometric plane, the second distance being different from the first distance,
wherein a guide body is coupled to a side opposite to a side where the stationary unit and a rotary unit are coupled to each other, the guide body guiding the rotary unit as the rotary unit moves toward or away from the binding unit,
wherein the rotary unit includes a rotary cam that includes a concave cam recess and a convex cam projection, and
wherein the guide body includes a guide cam that includes a concave cam recess and a convex cam projection.

15. The rotary device of claim 14, wherein the rotary cam and the guide cam are rotatably engaged with each other, and as the rotary cam is rotated with respect to the guide cam, the cam projection of the rotary cam is moved between the cam recess and the cam projection of the guide cam in a sliding manner.

16. The rotary device of claim 15, wherein, when the rotary unit is located at the first position, the cam projection of the rotary cam is positioned adjacent to the cam recess of the guide cam between the cam recess and the cam projection of the guide cam, and when the rotary unit is located at the second position, the cam projection of the rotary cam is positioned adjacent to the cam projection of the guide cam between the cam recess and the cam projection of the guide cam.

17. The rotary device of claim 16, wherein the rotary unit includes an insertion part, into which at least a part of the stationary unit is inserted, and wherein a cylinder part formed on the stationary unit is inserted into the insertion part of the rotary unit,
a spring is inserted between the stationary unit and the rotary unit, in which one end of the spring is inserted into the cylinder part and another end is inserted into the insertion part, and
the spring provides an elastic force to the rotary unit or the stationary unit to bias the rotary unit in a direction away from the stationary unit.

18. The rotary device of claim 17, wherein the stationary unit further includes a stop recess including a first end and a second end, and the rotary unit includes a stop projection that engages one of the first end and the second end of the stop recess at the second position.

19. The rotary device of claim 18, further comprising:
a cam shaft that forms a rotary axis of the rotary unit, wherein the cam shaft includes a first end and a second end, the first end of the cam shaft being connected to the stationary unit and the second end of the cam shaft being connected to the guide cam.

20. An electronic device comprising a rotary device, wherein the rotary device comprises: a binding unit configured to be coupled to an external object; a stationary unit coupled to the binding unit; a rotary unit rotatably coupled to the stationary unit, the rotary unit configured to be fixed among a plurality of set positions with respect to the stationary unit; wherein as the rotary unit is rotated with respect to the stationary unit, the rotary unit is sequentially moved toward or away from the binding unit at the plurality of positions; the rotary device includes a main body coupled to the rotary unit, and the main body includes a coupling part coupled to the rotary unit, and at least one module mounted thereon, wherein the stationary unit includes: a stop pin and a pin installation part, the pin being inserted into the in installation part, and further comprising a spring configured to provide an elastic force to the stop pin, and wherein a through hole is formed in the pin installation part to extend to an outer circumferential surface of the stationary unit, the stop pin being positioned through the through hole and one end of the stop pin protruding from the outer circumferential surface of the stationary unit.

21. The electronic device of claim 20, wherein the at least one module is operated when positioned at an operation position set among the plurality of positions.

22. The electronic device of claim 20, wherein the at least one module includes at least one of a bone conduction speaker and a Heart Rate Monitor (HRM).

23. The electronic device of claim 22, wherein the main body further includes a camera, and
   the camera is operated at a first position when the rotary unit forms a first angle with a part of the external object.

* * * * *